United States Patent
Milne et al.

(10) Patent No.: US 6,559,261 B1
(45) Date of Patent: May 6, 2003

(54) POLYMER PRODUCTION

(75) Inventors: Paul E Milne, Malvern (GB); Keith M Blackwood, Bracknell (GB)

(73) Assignee: QinetiQ Limited, Farnborough (GB)

( * ) Notice: Subject to any disclaimer, the term of this patent is extended or adjusted under 35 U.S.C. 154(b) by 0 days.

(21) Appl. No.: 09/743,901

(22) PCT Filed: Jul. 26, 1999

(86) PCT No.: PCT/GB99/02448

§ 371 (c)(1),
(2), (4) Date: Jan. 17, 2001

(87) PCT Pub. No.: WO00/06610

PCT Pub. Date: Feb. 10, 2000

(30) Foreign Application Priority Data

Jul. 25, 1998 (GB) ................................. 9816167

(51) Int. Cl.[7] .............................. C08F 126/00
(52) U.S. Cl. ................ 526/312; 526/279; 526/287; 526/288; 526/303.1; 526/311
(58) Field of Search ................ 526/279, 287, 526/288, 303.1, 311, 312

(56) References Cited

U.S. PATENT DOCUMENTS

| | | |
|---|---|---|
| 3,888,928 A | 6/1975 | Lang et al. |
| 3,912,693 A | 10/1975 | Shimizu et al. |
| 4,121,986 A | 10/1978 | Battaerd |
| 4,988,753 A | 1/1991 | Rullmann et al. |

FOREIGN PATENT DOCUMENTS

| | | |
|---|---|---|
| EP | 0 103 225 | 3/1984 |
| EP | 0547555 | 6/1993 |
| EP | 0 548 826 | 6/1993 |
| EP | 0 969 028 A2 | 1/2000 |
| EP | 0 969 061 A2 | 1/2000 |
| EP | 0970 946 A2 | 1/2000 |
| FR | 2 109 692 | 5/1972 |

OTHER PUBLICATIONS

G. B. Butler et al.: "Preparation and polymerization of unsaturated Quaternary Ammonium Compounds. VII. Derivatives of 1,x–diamino–alkanes" Journal of the American Chemical Society., vol. 78, 1956, pp. 4797–4800, DC US.

G. B. Butler et al.: "Preparation and polymerization of unsaturated quaternary ammonium compounds. V. Propargyl derivatives" Journal of the American Chemical Society., vol. 76, 1954, pp. 713–714, DC US.

Marek, Miroslav, Jr. et al.: "Preparation of a multilayered film of ultrathin poly (tetraallylammonium bromide) network" Chem. Lett. (1993), 2 291–4, p. 292.

Primary Examiner—Helen L. Pezzuto
(74) Attorney, Agent, or Firm—Nixon & Vanderhye P.C.

(57) ABSTRACT

A method for producing a polymeric material, said method comprising subjecting a starting material which includes two multiple bonds which are activated so that they will take part in a polymerisation reaction and wherein the multiple bonds are sufficiently close togeter to ensure that cyclopolymerisation will preferentially occur; to suitable conditions under which said polymerisation reaction will occur, provided that the starting marerial is other than triallyamine hydrochloride. The method can be used to produce polymers for various processes including adhesives, network polymers, liquid crystal polymers etc.

25 Claims, No Drawings

POLYMER PRODUCTION

The present invention relates to methods of producing polymeric compounds, in particular using radiation curing such ultraviolet or thermal radiation, or chemical curing or electron beam initiated curing. Certain compounds which form polymers under the influence of u.v. light form a further aspect of the invention, as well as to polymers, coatings and adhesives obtained thereby.

The polymerisation of diallyamines using free radical initiation is known, for example from Solomon et al., J. Macromol. Sci.- Rev Macromol. Chem. c15 (1) 143–164 (1976). Free radical initiation of polymerisation requires quite extreme reaction conditions which can be generated only in production plants etc. It is not suitable for situations where in situ polymerisation is required.

Other cyclpolymerisation reactions are discussed by C. D. McLean et al., J. Macromol. Sci.-Chem., A10 (5), pp857–873 (1976). Yet further reactions are described in WO 97/16504, WO97/16472 where such reactions are used in a specialised way in the production of liquid crystal compounds.

The applicants have found that a broad range of compounds with at least two appropriately positioned multiple bonds and in particular double bonds may be activated by the presence of an electron withdrawing group, in particular where the electron withdrawing group is at a position which is alpha, beta or gamma to one or both of the double bonds to make them readily polymerisable under the influence of inter alia radiation. The term "readily polymerisable" means that the compounds will undergo polymerisation under moderate conditions of temperature and pressure (for example at room temperature and atmospheric pressure) in the presence of radiation and an initiator, in a period of less than 24 hours.

Polymeric compounds obtained therefrom include cyclic rings. These have many advantageous properties. In particular, the invention can be used to generate products such as adhesives (see copending British Patent application No 9816169.8), coatings, network polymers or conducting polymers (see copending British Patent Application No. 9816171.0) depending upon the other aspects of the structure of the starting materials.

In its broadest aspect, the invention provides a method for producing a polymeric material, said method comprising subjecting a starting material which includes two double bonds which are activated so that they will take part in a polymerisation reaction and wherein the double bonds are sufficiently close together to ensure that cyclopolymerisation will preferentially occur; to suitable conditions under which said polymerisation reaction will occur, provided that the starting material is other than triallyamine hydrochloride.

Specifically, the invention provides a method for producing a polymeric material, said method comprising subjecting a starting material which comprises a group of sub-formula (I)

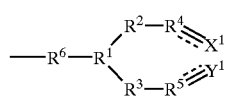

[I]

where
$R^1$ is $CR^a$ where $R^a$ is hydrogen of alkyl, and $R^6$ is a bond, or $R^1$ and $R^6$ together form an electron withdrawing group;

$R^2$ and $R^3$ are independently selected from $(CR^7R^8)_n$, or a group $CR^9R^{10}$, $CR^7R^8CR^9R^{10}$ or $CR^9R^{10}CR^7R^8$ where n is 0, 1 or 2, $R^7$ and $R^8$ are independently selected from hydrogen or alkyl, and either one of $R^9$ or $R^{10}$ is hydrogen and the other is an electron withdrawing group, or $R^9$ and $R^{10}$ together form an electron withdrawing group, and $R^4$ and $R^5$ are independently selected from CH or $CR^{11}$ where $R^{11}$ is an electron withdrawing group;

the dotted lines indicate the presence or absence of a bond, and $X^1$ is a group $CX^2X^3$ where the dotted line bond to which it is attached is absent and a group $CX^2$ where the dotted line bond to which it is attached is present, $Y^1$ is a group $CY^2Y^3$ where the dotted line bond to which it is attached is absent and a group $CY^2$ where the dotted line bond to which it is attached is present, and $X^2$, $X^3$, $Y^2$ and $Y^3$ are independently selected from hydrogen and fluorine;

provided that at least one of (a) $R^1$ and $R^6$ or (b) $R^2$ and $R^3$ or (c) $R^4$ and $R^5$ includes an electron withdrawing group which is able to activate a cyclopolymerisation reaction; to suitable conditions under which a cyclopolymerisation reaction will occur, subject to the following further provisos:

(i) that the starting material is other than triallyamine hydrochloride;

(ii) that when $R^1$ and $R^6$ together form the sole electron withdrawing group and $R^1$ is a group $N^+R^{12}$ $(Z^{m-})_{1/m}$, where $R^{12}$ is hydrogen or hydrocarbyl, Z is an anion of charge m and $R^6$ is a bond, said conditions are subjecting the compound to radiation in the substantial absence of a solvent or sulphur dioxide gas; and (iii) that where $R^1$ and $R^6$ together form the sole electron withdrawing group and $R^1$ is CH and $R^6$ is OC(O), then the compound does not further contain a mesogenic group, or contains at least one further group of sub-formula (I).

As used herein, the expression "in the substantial absence of solvent" means that there is either no solvent present or there is insufficient solvent present to completely dissolve the reagents, although a small amount of a diluent may be present to allow the reagents to flow.

Conditions under which polymerisation will occur include the influence of radiation or an electron beam, or in the presence of a chemical initiator. Radiation or electron beam induced polymerisation is suitably effected in the substantial absence of a solvent.

In particular $X^1$ and $Y^1$ are groups $CX^2X^3$ and $CY^2Y^3$ respectively and the dotted lines represent an absence of a bond. Thus preferred compounds are those of sub-formula (IA)

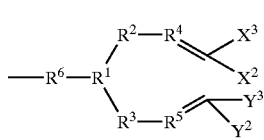

[IA]

where $R^1$, $R^2$, $R^3$, $R^4$, $R^5$, $R^6$, $X^2$, $X^3$, $Y^2$ and $Y^3$ are as defined above. One or more such starting materials may be polymerised together. When more than one starting material is used, a copolymer will result.

When the dotted bonds in sub formula (I) are present, the resulting polymer will comprise polyacetylene chains. This can lead to a conjugated system and consequently a conducting polymer.

Suitably there are no more than five atoms in between or linking the double bonds in the starting material so that when the cyclopolymerisation takes place, for example as illustrated hereinafter in FIG. 1, the size of the rings formed does not exceed 7. Preferably, there are from 3 to 5 atoms in between the double bonds.

Suitably the starting material is one which will cyclopolymerise in the sort of conditions used in polymer production. This may comprise the application of radiation such as uv or thermal radiation, where necessary in the presence of a photoinitiator, by the application of other sorts of initiator such as chemical initiators, or by initiation using an electron beam. The expression "chemical initiator" as used herein refers to compounds which can initiate polymerisation such as free radical initiators and ion initiators such as cationic or anionic initiators as are understood in the art.

Preferably, the starting materials polymerise under the influence of ultraviolet or thermal radiation, preferably ultraviolet radiation. Cyclopolymerisation may take place either spontaneously or in the presence of a suitable initiator. Examples of suitable initiators include 2,2'-azobisisobutyronitrile (AIBN), aromatic ketones such as benzophenones in particular acetophenone; chlorinated acetophenones such as di- or tri-chloroacetophenone; dialkoxyacetophenones such as dimethoxyacetophenones (sold under the Trade name "Irgacure 651"); dialkylhydroxyacetophenones such as dimethylhydroxyacetophenone (sold under the Trade name "Darocure 1173"); substituted dialkylhydroxyacetophenone alkyl ethers such compounds of formula

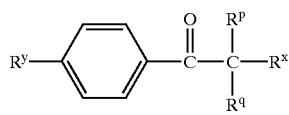

where $R^y$ is alkyl and in particular 2,2-dimethylethyl, $R^x$ is hydroxy or halogen such as chloro, and $R^p$ and $R^q$ are independently selected from alkyl or halogen such as chloro (examples of which are sold under the Trade names "Darocure 1116" and "Trigonal P1"); 1-benzoylcyclohexanol-2 (sold under the Trade name "Irgacure 184"); benzoin or derivatives such as benzoin acetate, benzoin alkyl ethers in particular benzoin butyl ether, dialkoxybenzoins such as dimethoxybenzoin or deoxybenzoin; dibenzyl ketone; acyloxime esters such as methyl or ethyl esters of acyloxime (sold under the trade name "Quantaqure PDO"); acylphosphine oxides, acylphosphonates such as dialkylacylphosphonate, ketosulphides for example of formula

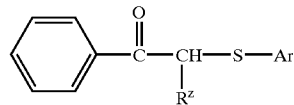

where $R^z$ is alkyl and Ar is an aryl group; dibenzoyl disulphides such as 4,4'-dialkylbenzoyldisulphide; diphenyldithiocarbonate; benzophenone; 4,4'-bis(N,N-dialkylamino)benzophenone; fluorenone; thioxanthone; benzil; or a compound of formula

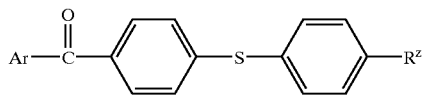

where Ar is an aryl group such as phenyl and $R^z$ is alkyl such as methyl (sold under the trade name "Speedcure BMDS")

As used herein, the term "alkyl" refers to straight or branched chain alkyl groups, suitably containing up to 20 and preferably up to 6 carbon atoms. The term "alkenyl" and "alkynyl" refer to unsaturated straight or branched chains which include for example from 2–20 carbon atoms, for example from 2 to 6 carbon atoms. Chains may include one or more double or triple bonds respectively. In addition, the term "aryl" refers to aromatic groups such as phenyl or naphthyl.

The term "hydrocarbyl" refers to any structure comprising carbon and hydrogen atoms. For example, these may be alkyl, alkenyl, alkynyl, aryl such as phenyl or napthyl, arylalkyl, cycloalkyl, cycloalkenyl or cycloalkynyl. Suitably they will contain up to 20 and preferably up to 10 carbon atoms. The term "heterocylyl" includes aromatic or non-aromatic rings, for example containing from 4 to 20, suitably from 5 to 10 ring atoms, at least one of which is a heteroatom such as oxygen, sulphur or nitrogen. Examples of such groups include furyl, thienyl, pyrrolyl, pyrrolidinyl, imidazolyl, triazolyl, thiazolyl, tetrazolyl, oxazolyl, isoxazolyl, pyrazolyl, pyridyl, pyrimidinyl, pyrazinyl, pyridazinyl, triazinyl, quinolinyl, iosquinolinyl, quinoxalinyl, benzthiazolyl, benzoxazolyl, benzothienyl or benzofuryl.

The term "functional group" refers to reactive groups such as halo, cyano, nitro, oxo, $C(O)_nR^a$, $OR^a$, $S(O)_tR^a$, $NR^bR^c$, $OC(O)NR^bR^c$, $C(O)NR^bR^c$, $OC(O)NR^bR^c$, $-NR^7C(O)_nR^6$, $-NR^aCONR^bR^c$, $-C=NOR$, $-N=CR^bR^c$, $S(O)_tNR^bR^c$, $C(S)_nR^a$, $C(S)OR^a$, $C(S)NR^bR^c$ or $-NR^bS(O)_tR^a$ where $R^a$, $R^b$ and $R^c$ are independently selected from hydrogen or optionally substituted hydrocarbyl, or $R^b$ and $R^c$ together form an optionally substituted ring which optionally contains further heteroatoms such as $S(O)_s$, oxygen and nitrogen, n is an integer of 1 or 2, t is 0 or an integer of 1–3. In particular the functional groups are groups such as halo, cyano, nitro, oxo, $C(O)_nR^a$, $OR^a$, $S(O)_tR^a$, $NR^bR^c$, $OC(O)NR^bR^c$, $C(O)NR^bR^c$, $OC(O)NR^bR^c$, $-NR^7C(O)_nR^6$, $-NR^aCONR^bR^c$, $-NR^aCSNR^bR^c$, $-C=NOR^a$, $-N=CR^bR^c$, $S(O)_tNR^bR^c$, or $-NR^bS(O)_tR^a$ where $R^a$, $R^b$ and $R^c$, n and t are as defined above.

The term "heteroatom" as used herein refers to non-carbon atoms such as oxygen, nitrogen or sulphur atoms. Where the nitrogen atoms are present, they will generally be present as part of an amino residue so that they will be substituted for example by hydrogen or alkyl.

The term "amide" is generally understood to refer to a group of formula $C(O)NR^aR^b$ where $R^a$ and $R^b$ are hydrogen or an optionally substituted hydrocarbyl group. Similarly, the term "sulphonamide" will refer to a group of formula $S(O)_2NR^aR^b$.

AS described above, suitable starting materials for use in the method of the invention will comprise a group of sub-formula (I)

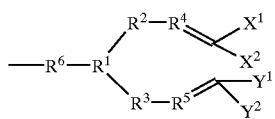

where
- $X^1$, $X^2$, $Y^1$ and $Y^2$ are independently selected from hydrogen or fluorine, $R^1$ is $CR^a$ where $R^a$ is hydrogen or alkyl, and $R^6$ is a bond, or $R^1$ and $R^6$ together form an electron withdrawing group;
- $R^2$ and $R^3$ are independently selected from $(CR^7R^8)_n$, or a group $CR^9R^{10}$, —$(CR^7R^8CR^9R^{10})$— or —$(CR^9R^{10}CR^7R^8)$— where n is 0, 1 or 2, $R^7$ and $R^8$ are independently selected from hydrogen or alkyl, and either one of $R^9$ or $R^{10}$) is hydrogen and the other is an electron withdrawing group, or $R^9$ and $R^{10}$ together form an electron withdrawing group, and
- $R^4$ and $R^5$ are independently selected from CH or $CR^{11}$ where $R^{11}$ is an electron withdrawing group;
- provided that at least one of (a) $R^1$ and $R^6$ or (b) $R^2$ and $R^3$ or (c) $R^4$ and $R^5$ includes an electron withdrawing group.

The nature of the electron withdrawing group or groups used in any particular case will depend upon its position in relation to the double bond it is required to activate, as well as the nature of any other functional groups within the compound.

In a preferred embodiment, $R^1$ and $R^6$ form an electron withdrawing group. For example, $R^1$ is a heteroatom or a substituted heteroatom which has electron withdrawing properties, for example a group $N^+R^{12}$ $(Z^{m-})_{1/m}$, $S(O)_pR^3$, B, $P(O)_qR^{14}$ or $Si(R^{15})$ where $R^{12}$, $R^{13}$, $R^{14}$ and $R^{15}$ are independently selected from hydrogen or hydrocarbyl, Z is an anion of charge a, p is 0, 1 or 2, and q is 1; and $R^6$ is a bond: or $R^1$ is a group CH and $R^6$ is a group —C(O)O— or —OC(O)—. Most preferably, $R^1$ is a group $N^+R^{12}$ $(Z^{m-})_{1/m}$, $S(O)_pR^{13}$, B, $P(O)_qR^{14}$ or $Si(R^{15})$ where $R^{12}$, $R^{13}$, $R^{14}$ and $R^{15}$ are independently selected from hydrogen or alkyl in particular $C_{1-3}$ alkyl, and Z is an anion, preferably a halide. In particular $R^1$ is a group $N^+R^{12}$ $(Z^{m-})_{1/m}$, and $R^6$ is a bond.

The nature of the anion Z will affect the properties of the final polymer and in particular, its conductivity, porosity and water permeability. Suitable anions for the Z group include halide ions such as fluoride, chloride, bromide or iodide, borides such as boron tetrafluoride; carboxylic acid esters such as those of formula $R^{14}C(O)O$— where $R^{14}$ is an optionally substituted hydrocarbyl group group such as haloalkyl, in particular trifluoromethyl; and other cationic groups such as mesylate and tosylate. In general, the water permeability of the ultimate polymer will vary as follows:

Other factors which affect the water permeability of the polymer is the nature of any group to which the group of sub-formula (I) is attached. When this contains for example perhaloalkyl substituents such as perfluoroalkyl, it will be largely water impermeable as compared to polymers which have alkylene bridging groups optionally interposed with say oxygen. Examples of such groups are given below.

Most preferably, the combination of $R^1$ and $R^6$ forms an amide group, where $R^1$ is a nitrogen atom and $R^6$ is a carbonyl group. In a further preferred embodiment, $R^1$ and $R^6$ together form a sulphonamide group where $R^1$ is a nitrogen atom and $R^6$ is an $S(O)_2$ group.

Alternatively, where the activation is effected by electron withdrawing groups at a position indicated by $R^2$ or $R^3$, suitable electron withdrawing groups $R^9$ and $R^{10}$ include nitrile, trifluoromethyl, acyl such as acetyl or nitro, or preferably $R^9$ and $R^{10}$ together with the carbon atom to which they are attached form a carbonyl group.

Where $R^{11}$ is an electron withdrawing group, it is suitably acyl such as acetyl, nitrile or nitro.

Preferably $X^1$, $X^2$, $Y^1$ and $Y^2$ are all hydrogen.

Suitable groups $R^a$ include hydrogen or methyl, in particular hydrogen.

A preferred group of the compounds for use in the method of the invention is a compound of structure (II)

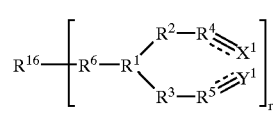

and in particular a compound of formula (IIA)

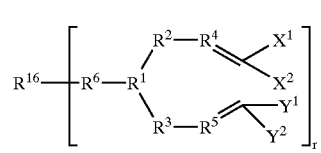

where $X^1$, $X^2$, $X^3$, $Y^1$, $Y^2$, $Y^3$, $R^1$, $R^2$, $R^3$, $R^4$, $R^5$, $R^6$ and the dotted bonds are as defined in relation to formula (I) above, r is an integer of 1 or more, and $R^{16}$ is a bridging group, an optionally substituted hydrocarbyl group, a perhaloalkyl group or an amide, of valency r.

Where in the compound of formula (II) and (IIA), r is 1, compounds can be readily polymerised to form a variety of polymer types depending upon the nature of the group $R^{16}$ and examples of groups which are commonly found in polymer technology is included below in Table 1. Some may be able to act, for example, as radiation curable adhesives as described in copending British Patent application No 9816169.8.

However, other applications for such polymers obtained using the process of the invention may be found.

Monomers of this type may be represented as structure (III)

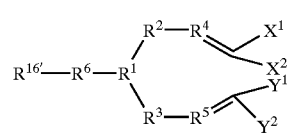

where $X^1$, $X^2$, $Y^1$, $Y^2$, $R^1$, $R^2$, $R^3$, $R^4$, $R^5$ and $R^6$ are as defined in relation to formula (I) above, $R^{16}$ is an optionally substituted hydrocarbyl group, a perhaloalkyl group or an amide.

Preferably in the compounds of formula (III), as above, $R^1$ and $R^6$ form an electron withdrawing group. Suitably then $R^2$ and $R^3$ are groups $(CR^7R^8)$ n and $R^4$ and $R^5$ are CH groups. Suitably, in the case of adhesives, $R^{16}$ comprises a hydrocarbyl group, optionally substituted by a functional group. Preferably $R^7$ includes an unsaturated moiety, such as an aryl or alkenyl group, or a carbonyl substituent.

A class of compounds of formula (III) are those of formula

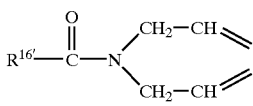

[IV]

where $R^6$ is as defined above, and is in particular an optionally substituted alkyl, alkenyl, alkynyl or aryl group, wherein the optional substituents may be selected from halogen, hydroxy, carboxy or salts thereof or acyloxy. These compounds may be used in the monomer form as adhesive compositions. However, pre-formed polymers obtained by polymerisation of these monomers form an aspect of the present invention.

Alternatively, $R^{16'}$ in formula (IV) may comprise a perhaloalkyl group, for example of from 1 to 3 carbon atoms such as a perhalomethyl group, in particular perfluoromethyl. Another group for $R^{16'}$ in formula (IV) is a dialkenyl substituted amide, for example of sub formula (V)

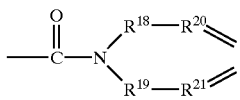

(V)

where $R^{18}$ and $R^{19}$ are selected from groups defined above for $R^2$ and $R^3$ in relation to formula (I), and are preferably —CH$_2$— or —CH$_2$CH$_2$— groups; and $R^{20}$ and $R^{21}$ are selected from groups defined above as $R^3$ and $R^4$ in relation to formula (I) and are preferably —CH— groups. Such groups would further activate the double bonds and give rise to the possibility of forming cross-linked polymer networks.

Another class of compound of formula (II) is represented by radiation curable compounds of formula (VI)

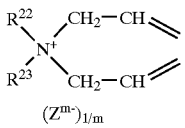

[VI]

where Z and m are as defined above, $R^{22}$ and $R^{23}$ are independently selected from hydrogen and hydrocarbyl, such as alkyl and alkenyl, in particular prop-2-enyl or hydroxyethyl.

The invention may also be applied to other sorts of polymers, for example, where in the compounds of formula (II), r is greater than one, polymerisation can result is polymer networks. Particular examples are compounds of formula (II) as defined above, where $R^{16}$ is a bridging group and r is an integer of 2 or more, for example from 2 to 8 and preferably from 2–4.

On polymerisation of these such compounds, networks are formed whose properties may be selected depending upon the precise nature of the $R^{16}$ group, the amount of chain terminator present and the polymerisation conditions employed. Polymerisation will occur in accordance with the general scheme set out in FIG. 1 hereinafter.

Suitably r is an integer of from 2 to 6, preferably from 2 to 4. The polymers produced can be useful in a number of different applications including the production of network polymers and those used in thermal management. Such applications are described and claimed in copending British Patent application No. 9816171.0.

Thermal management is the control of optical properties of materials across solar and thermal wavebands (~0.7–12microns). This control of transmitted, reflected and absorbed radiation gives the potential to design systems that can selectively perform different tasks at different wavelengths. For example use of silver coatings by the glazing industry to limit solar transmission (material transparent at visible wavelengths but reflective across the solar) and thus prevent 'greenhouse' heating. Other example could be solar water heaters where the material is transparent at NIR wavelengths but reflective at longer wavelengths. Benefits of thermal management could be in reduced air conditioning/heating costs.

The properties of the polymer obtained in this way will depend upon a variety of factors but will depend very largely on the nature of the group $R^{16}$.

Suitably $R^{16}$ will comprise a bridging groups for example as is known in polymer, paint or coating chemistry. These may include straight or branched chain alkyl groups, optionally substituted or interposed with functional groups or siloxane groups such as alkyl siloxanes. Suitable bridging groups include those found in polyethylenes, polypropylenes, nylons, as listed in Table 1.

TABLE 1

| Polymer type | Repeat Unit of Bridging Group |
|---|---|
| Polyethylene | CH$_2$ |
| Polystyrene | CH$_2$CH(C$_6$H$_5$) where the phenyl ring is optionally substituted |
| Polyisobutylene | CH$_2$CH(CH(CH$_3$)$_2$) |
| Polyisoprene | CH$_2$CH(CH$_3$) |
| Polytetrafluoroethylene | CH$_2$(CF$_2$)$_x$CH$_2$ |
| Polyvinylidenefluoride | CH$_2$(CF$_2$CH$_2$)$_x$ |
| polyethyleneoxide | (OCH$_2$CH(CH$_3$))$_x$O |
| Nylon | CH$_2$(NHCOCH$_2$)$_x$CH$_2$ |
| Peptide | CH$_2$(NHCOCH$_R$)$_x$CH$_2$ |
| Polyurethanes | —NH—CO—O— |
| Polyesters | —RC(O)OR'— where R and R' are organic groups such as hydrocarbyl |
| Polysiloxanes | e.g. —SiO$_2$—, —R$_2$SiO— or —R$_2$Si$_2$O$_3$— where R is an organic group such as hydrocarbyl |
| Polyacrylates | —CH$_2$C(COOH)H— |
| Polyureas | —NHCONH— |
| Polythioureas | —NH—C(S)—NH— |

The length of the bridging group will affect the properties of the polymeric material derived from this. This can be used to design polymers with properties which are best suited to the application. For instance when the bridging group comprises relatively long chains, (for example with in excess of 6 repeat units, for example from 6–20 repeat units), the polymer will have pliable plastic properties. Alternatively, when the bridging group is relatively short, (e.g. less than 6 repeat units) the material will be more brittle.

Another method for producing particular properties arises from the possibility of producing copolymers where another monomeric compound, for example one which is not of formula (I), is mixed with the compound of formula (I) prior to polymerisation. Such monomers are known in the art.

Composites may also be produced by polymerising compounds of formula (I) in the presence of other moieties such as graphite, ethers such as crown ethers or thioethers, phthalocyanines, bipyridyls or liquid crystal compounds, all of which will produce composite polymers with modified properties.

Examples of possible bridging groups $R^{16}$ where r is 2 are groups of sub-formula (VII)

$$-Z^1-(Q^1)_a-(Z^2-Q^2)_b-Z^3- \quad (VII)$$

where a and b are independently selected from 0, 1 or 2, $z_1$, $Z^2$ and $Z^3$ are independently selected from a bond, an optionally substituted linear or branched alkyl or alkene chain wherein optionally one or more non-adjacent carbon atoms is replaced with a heteroatom or an amide group, $Q^1$ and $Q^2$ are independently selected from an optionally substituted carbocylic or heterocyclic ring which optionally contains bridging alkyl groups.

Suitable carbocyclic rings for $Q^1$ and $Q^2$ include cycloalkyl groups for example from 1 to 20 carbon atoms. Bridged carbocylic ring structures include 1,4-bicyclo [2.2.2] octane, decalin, bicyclo[2.2.1]heptane, cubane, diadamantane, adamantane. Suitable heterocyclic rings include any of the above where one or more non adjacent carbon atoms are replaced by a heteroatom such as oxygen, sulphur or nitrogen (including amino or substituted amino), or a carboxyl or an amide group. Suitable optional substitutents for the groups $Q^1$ and $Q^2$ include one or more groups selected from alkyl, alkeny, alkynyl, aryl, aralkyl such as benzyl, or functional groups as defined above. Substitutents for the groups $Q^1$ and $Q^2$ are oxo and halogen in particular fluorine and chlorine.

Suitable optional substituents for the alkyl and alkene groups $Z^1$, $Z^2$ and $Z^3$ include aryl, aralkyl and functional groups as defined above. Particular substituents include halogen such as fluorine and chlorine, and oxo.

Other sorts of bridging groups $R^{16}$ include electrically conducting chains, for instance, electrically conducting unsaturated chains such as alkenes or chains incorporating aromatic or heterocyclic rings. For instance, the group $R^{16}$ may comprise a tetra substituted conducting unit such as a tertathiafulvalene. Thus an example of such a is a compound of formula (VIII)

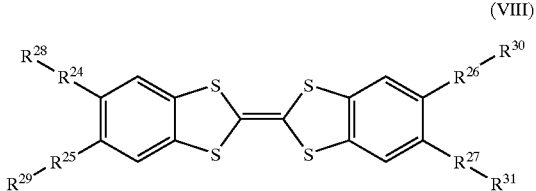

(VIII)

where $R^{28}$, $R^{29}$, $R^{30}$ and $R^{31}$ are each groups of sub-formula (IX)

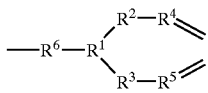

[IX]

where $R^1$, $R^2$, $R^3$, $R^4$, $R^5$ and $R^6$ are as defined in relation to formula (I) above and $R^{24}$, $R^{25}$, $R^{26}$ and $R^{27}$ are independently selected from groups of sub-formula (II) as given above. In particular $R^{24}$, $R^{25}$, $R^{26}$ and $R^{27}$ are alkyl groups.

Polymerisation of compounds of formula (III) will give cross-linked networks where the cross-linking occurs through the double bonded units. This will lead to a very stable material with robust physical properties. Once again, varying the length of the spacer groups $R^{24}$, $R^{25}$, $R^{26}$ and $R^{27}$ will lead to materials with designer properties. For instance when $R^{24}$, $R^{25}$, $R^{26}$ and $R^{27}$ are relatively long chains, the polymer will have pliable plastic properties. Alternatively, when the chains $R^{24}$, $R^{25}$, $R^{26}$ and $R^{27}$ are relatively short, the material will be more brittle.

Where $R^1$ and $R^6$ together form a group —N'R$^7$Z$^-$, varying the counter ion Z can also be used to adjust the physical properties of the polymer, such as water retention, porosity or conductivity. Suitably substituted materials will exhibit conducting properties, making them suitable as organic semiconductors for example for use as interconnects for IC chips etc.

Alternatively, a bridging group $R^{16}$ may comprise a tetra or octa substituted non-linear optic unit such as an optionally substituted porphyrin or phthalocyanine wherein the optional substitutents include hydrocarbyl groups as well as groups of sub formula (I). An example of such a porphyin compound is a compound of formula (X)

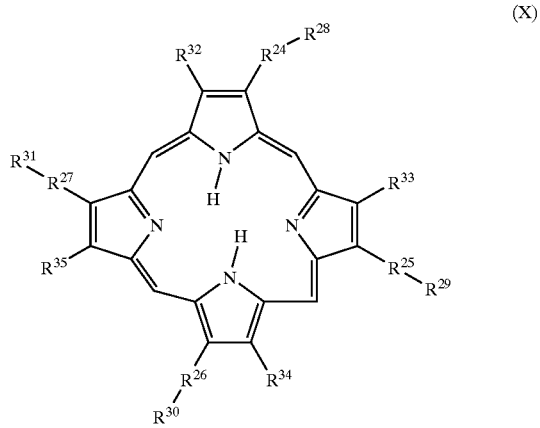

(X)

where $R^{24}$, $R^{25}$, $R^{26}$, $R^{27}$, $R^{28}$, $R^{29}$, $R^{30}$ and $R^{31}$ are as defined in relation to formula (III) above and $R^{32}$, $R^{33}$, $R^{34}$ and $R^{35}$ are each independently selected from hydrogen or hydrocarbyl groups; and the compound optionally contains a metal ion within the macrocyclic heterocyclic unit.

An alternative phthalocyanine compound is a compound of formula (XA)

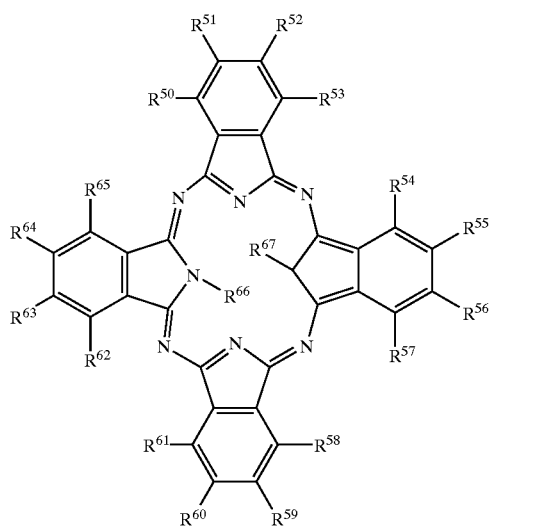

(XA)

where $R^{50}$ through to $R^{65}$ are independently selected from hydrocarbyl in particular $C_{1-12}$ alkyl, a group $OR^{68}$ where $R^{68}$ is hydrocarbyl in particular butyl, halogen in particular chlorine or a group $R^{24}$–$R^{28}$ where $R^{24}$ and $R^{28}$ are as defined in relation to formula (III) above, provided that at least two of $R^{50}$ to $R^{65}$ are $R^{24}$–$R^{28}$ groups, and $R^{66}$ and $R^{67}$ are either hydrogen or together comprise a metal ion such as a copper ion.

Preferably in formula (XA), $R^{51}$, $R^{52}$, $R^{55}$, $R^{56}$, $R^{59}$, $R^{60}$, $R^{63}$ and $R^{64}$ are halogen and $R^{50}$, $R^{53}$, $R^{54}$, $R^{57}$, $R^{58}$, $R^{61}$, $R^{62}$ and $R^{65}$ are independently $C_{1-12}$ alkyl, $C_{1-12}$ alkoxy or a group $R^{24}$–$R^{28}$ Polymerisation of a compound of formula (X) or (XA) in accordance with the scheme of FIG. 1, for example by photopolymerisation will provide a cross linked network polymer where the cross linking occurs through the diene units for example as either quaternery ammonium salts or amides depending upon the particular nature of the groups $R^1$ and $R^6$ present in the $R^{28}$, $R^{29}$, $R^{30}$ and $R^{31}$ units. Again this can produce a very stable network or elastomeric material with robust physical properties. In addition to conductivity, these polymers will be capable of exhibiting third order polarisabilities and be suitable for applications which employ the Kerr effect. These properties can be affected or moderated when metals or metal ions are inserted into the macrocyclic heterocyclic unit. Suitable metal ions include sodium, potassium, lithium, copper, zinc or iron ions.

Yet a further possibility for the bridging group $R^{16}$ is a polysiloxane network polymer where $R^{16}$ comprises a straight or branched siloxane chain of valency r or a cyclic polysiloxane unit.

Thus compounds of structure (XI)

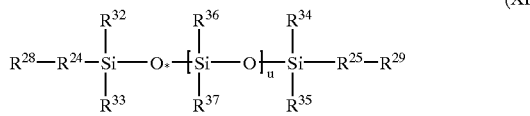

(XI)

where $R^{24}$, $R^{25}$, $R^{28}$ and $R^{29}$ are as defined above in relation to formula (VII), $R^{32}$, $R^{33}$, $R^{34}$ are $R^{35}$, are selected from hydrocarbyl such as alkyl and in particular methyl, and each $R^{36}$ or $R^{37}$ group is independently selected from hydrocarbyl or a group of formula $R^6$–$R^{30}$ where $R^{26}$ and $R^{30}$ are as defined above in relation to formula (VII), and u is 0 or an integer of 1 or more, for example of from 1 to 20; and (XII).

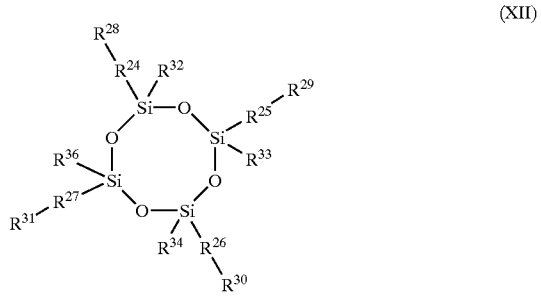

(XII)

where $R^{24}$, $R^{25}$, $R^{26}$, $R^{27}$, $R^{28}$, $R^{29}$, $R^{30}$ and $R^{31}$ are as defined above in relation to formula (VII) and $R^{32}$, $R^{33}$, $R^{34}$ and $R^{35}$ are as defined above in relation to formula (XI). Although formula (XII) has been illustrated with four siloxane units in the ring, it will be appreciated that there may be other numbers of such units in the cyclic ring, for example from 3 to 8, preferably from 3 to 6 siloxane units.

In the above structures (XI) and (XII), it will be appreciated that —Si— may be replaced by B or B$^-$; or —Si—O— is replaced by —B—N($R^{39}$)— where $R^{39}$ is a hydrocarbyl group such as those defined above in relation to group $R^{32}$ in formula (XI) or a group —$R^{24}$–$R^{28}$ as defined in relation to formula (XII) above.

Upon polymerisation, compounds of formula (XI) and (XII) or variants thereof, will form a cross-linked network where the cross-linking occurs through the groups $R^{28}$, $R^{29}$, $R^{30}$ and $R^{31}$ as illustrated in FIG. 1. Such polymers may exhibit properties similar to those of conventional siloxanes. However, in the case of compounds of formula (XI) and (XII), they may be coated onto surfaces and polymerised in situ, for example using radiation curing.

Further examples of compounds of formula (III) include compounds of formula (XIII)

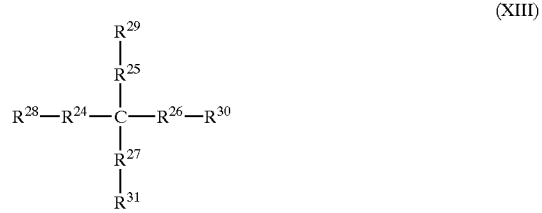

(XIII)

where $R^{24}$, $R^{25}$, $R^{26}$, $R^{27}$, $R^{28}$, $R^{29}$, $R^{30}$ and $R^{31}$ are as defined above in relation to formula (VIII).

The methodology of the invention may also be applied to the production of liquid crystal polymers. In this case, the monomeric units will include a mesogenic group as is understood in the art.

For example, suitable polymers may be obtained by the polymerisation of compounds of formula (III) where $R^{16}$ comprises a group of sub formula (XIV)

$R^{33}$—$Z^6$—$R^{24}$— (XIV)

where $R^{24}$ is as defined above, $Z^6$ is selected from O, S, single covalent bond, COO, OCO; and $R^{33}$ represents any mesogenic group;

Compounds of this type are novel and form the subject of a copending patent application of the applicants.

Compounds of formula (II) are suitably prepared by conventional methods, for example by reacting a compound of formula (XV)

[XV]

where $X^1$, $Y^1$, $Y^2$, $R^2$, $R^2$, $R^3$, $R^4$, $R^5$ and the dotted bonds are as defined in relation to formula (II), $R^{1'}$ is a group $R^1$ as defined in formula II or a precursor thereof, and $R^{40}$ is hydrogen or hydroxy, with a compound of formula (XVI)

$R^{16}$—[$R^6$—$Z^4$]$_r$ (XVI)

where $R^6$, $R^{16}$ and r are as defined in relation to formula (II) and $Z^4$ is a leaving group, and thereafter if necessary, converting a precursor group $R^{1'}$ to a group $R^1$.

Where a compound of formula (IIA) is produced, the compound of formula (XV) will be of formula (XVA)

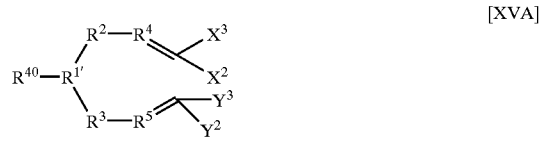

[XVA]

where $R^{1'}$, $R^2$, $R^3$, $R^4$, $R^5$, $R^{40}$, $X^2$, $X^3$, $Y^2$ and $Y^3$ are as defined above.

Suitable leaving groups $Z^4$ include halogen in particular bromo, mesylate or tosylate. The reaction is suitably effected in an organic solvent such as tetrahydrofuran, dichloromethane, toluene, an alcohol such as methanol or ethanol, or a ketone such as butanone and at elevated temperatures for example near the boiling point of the solvent.

Preferably the reaction is effected in the presence of a base such as potassium carbonate.

When the group $R^{1'}$ is a precursor of the group $R^1$, it may be converted to the corresponding $R^1$ group using conventional techniques. For example $R^{1'}$ may be a nitrogen atom, which may be converted to a group $NR^{12}$ $(Z^{m-})_{1/m}$ where $R^{12}$, Z and m are as defined above, by reaction with an appropriate salt under conventional conditions. Examples of this are illustrated hereinafter.

Compounds of formulae (XV) and (XVI) are either known compounds or they can be prepared from known compounds by conventional methods.

During the polymerisation process, the compounds link together by way of the multiple bond, in particular the diene group as illustrated in FIG. 1. Where the compounds used include more than one diene grouping, for example compounds of formula (II) where R is 2 or more, they will tend to become cross linked to form a network or three dimensional structure. The degree of cross linking can be controlled by carrying out the polymerisation in the presence of cross-linkers, where for example r is greater than 2, for example 4, or diluents. The latter will suitably comprise a compound of formula (XVI)

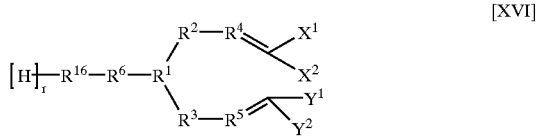

[XVI]

where $X^1$, $X^2$, $Y^1$, $Y^2$, $R^1$, $R^2$, $R^3$, $R^4$, $R^5$, $R^6$, $R^{16}$ and r are as defined in relation to formula (II).

The method of the invention can be used in the preparation of homopolymers or copolymers where they are mixed with other monomeric units, which may themselves be of a similar basic structure, for example of formula (II) or otherwise.

A general scheme illustrating the sort of polymerisation process which may occur using a polyethylene type bridging group is illustrated in FIG. 2.

Using the method of the invention, it is possible to take a suitable organic system that has optimal or optimised properties for use in certain applications, e.g. high yield strength, large hyperpolarisability, high pyroelectric coefficient, high conductivity etc. and to structurally modify the system so that it is possible to polymerise it. If functional groups are incorporated that will polymerise, it will become possible to create a three dimensional network or plastic that will have properties associated with the parent organic system.

The advantages of the compounds of the invention is that they allow for the possibility that they can be applied in the form of a paint and caused to polymerise in situ. Thus this allows for ease of processing. Further, by providing for the construction of networks as a result of the cross linking, the resultant polymer can be mechanically strong and durable.

The versatility of the systems of the invention mean that it is possible to build in anisotropy which would improve directional physical properties, e.g. NLO, mechanical yield strength etc. Both amorphous or ordered systems can be prepared depending upon the particular polymerisation conditions used.

Copolymerisation is also possible and this can be used advantageously to affect physical properties of the polymer obtained.

Polymers obtained using the method of the invention maybe particularly suitable for the production of adhesive coatings, and multilayer coatings as well as binders. It is possible to manipulate the low molar mass coating before polymerisation is carried out, e.g., poling etc.

Films of polymeric material can be prepared as illustrated hereinafter. Thus material with the properties of for example, polyethylene films can be produced using radiation curing techniques if required.

Polymer coatings prepared as described herein have useful water-proofing, corrosion resistance and general dust and dirt protective properties, in particular where they include halogenated and particularly fluorinated bridging groups. Thus they may be used in the production of fabrics such as clothing, electrical components or devices, mechanical components as well as building materials which require this feature. In addition, coatings of this type may produce anti-icing features which are useful, particularly where these materials are exposed to harsh external conditions. Products treated in this way also exhibit strong pearling qualities and this assists in the rapid shedding of condensate. Thus surfaces remain relatively free of such condensates.

Such surfaces can be achieved on at least part of the internal surfaces of a structure containing interconnecting interstitial spaces, such as fibrous or granular material. The present invention provides a product selected from a fabric, an electrical component or device, a mechanical component, or a construction or building material, having deposited thereon a polymeric coating derived from a monomer of formula (I) as defined above.

Suitable electrical components include small electrical components such as resistors, capacitors, condensers, circuit breakers, switches and connectors, as well as small assemblies of these, for example circuit boards on which these and/or other components are mounted. Electrical devices include conductors, such as HT leads for example, those used in automobile engines, and cables such as external or underground power cables. Such cables may be pre-coated with plastics of another insulating material.

Plastics coatings in accordance with the invention may be applied to electrical wiring. In particular, monomers of formula (I) which mimic polypropylene would be useful in this context.

Mechanical components include housings, bearings, shafts, gears, wheels, gaskets, filter housing, engines, gearboxes, transmission, steering or suspension components.

Building materials include wood, brick, concrete slabs or other pre-formed concrete structures, building blocks, stone, slates or insulation materials where there is a possibility that corrosion, weathering or water penetration is likely to cause problems.

Polymer coatings formed in accordance with the invention may be useful in electronic components which have a polymeric coating as resistance layers. The nature of the bridging group $R^{16}$ will affect the resistance of the polymer layer.

Optionally the bridging groups in the monomers may be aromatic or heteroaromatic, i.e. it may include one or more unsaturated carbon rings, optionally containing heteroatoms such as nitrogen, oxygen or sulphur, which give the surface formed additional resistance to etching by plasma etch processes as used in the semiconductor integrated circuit industry.

If necessary, the coating may be discontinuous, for example, patterned by etching, optionally after masking certain areas, so as to provide the desired electronic properties. Techniques for achieving this are well known, and include for example, irradiation with high energy radiation such as electron beams, X-rays or deep ultraviolet rays.

The irradiation breaks the bonds in the polymer and exposed areas can then be dissolved in a developer liquid. Optionally, the coating may consist of a mixture of a monomer and a chemical designed to enhance its sensitivity to radiation exposure during the patterning process, such as quinione diazide or anthraquinone.

Suitable electronic components include printed circuit boards, semiconductor elements, optical devices, videodiscs, compact discs, floppy discs and the like.

EXAMPLE 1

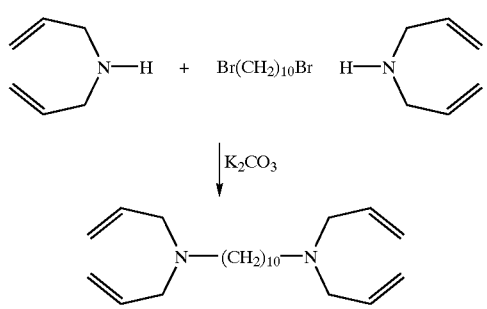

Diallylamine (6.45 g, 0.66 mol), 1,10-dibromodecane (10.0 g, 0.033 mol) and potassium carbonate 9.70 g, 0.66 mol) were placed in ethanol (60 cm$^3$) and the mixture was refluxed for 10 hours. The solids were removed by filtration and the solvent removed in vacuo to leave a yellow oil. The oil was purified by column chromatography using silica gel and ethyl acetate to leave, after removal of solvent in vacuo, 9.80 g, 89% of yellow oil.

$^1$HNMR (CDCl$_3$) δ: 1.15–1.30 (m, 12H), 1.35–1.45 (m, 4H), 2.40 (t, 4H), 3.10 (d, 8H), 5.05–5.20 (m, 8H), 5.30–5.55 (m, 4H).

Ir vmax (thin film): 2920, 2850, 2800, 1640, 1460, 1440, 1350, 1250, 1150, 1110, 990, 915 cm$^{-1}$.

Step 2

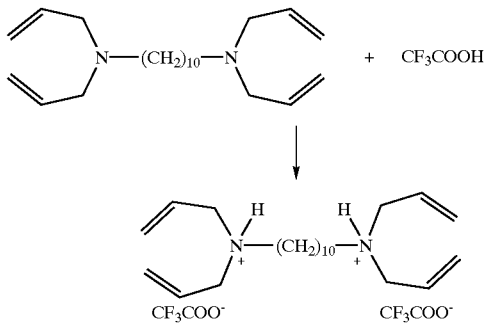

The monomer from step 1 above (4.0 g) was treated with 3M aqueous methanolic trifluoroacetic acid to pH 1.0. The organic phase was extracted with dichloromethane (100 cm$^3$) and washed with brine (60 cm$^3$) and water (60 cm$^3$) and then dried over MgSO$_4$. Removal of solvent left a yellow oil. 6.4 g, 95%.

$^1$HNMR (CDCl$_3$) δ: 1.30 (m, 12H), 1.65 (quin, 4H), 3.0 (quin, 4H), 3.72 (s, 8H), 5.60 (m, 8H), 5.90 (m, 4H), 10.10 (s, 2H).

Ir vmax (KCl disc): 2934, 2861, 1780, 1669, 1428, 1169.3 (s), 994.5, 950.8, 798, 722, 706, 617 cm$^{-1}$.

Step 3

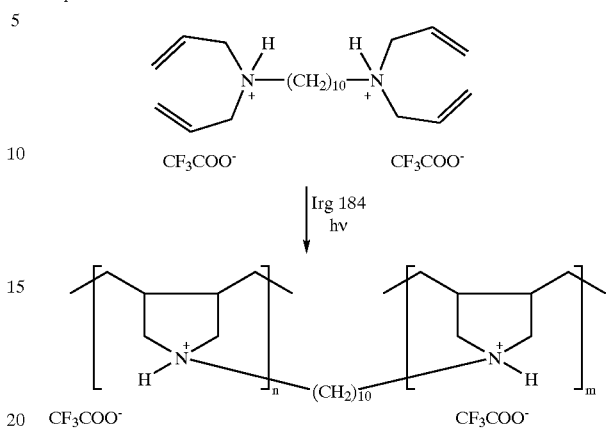

The monomer from step 2 above (0.2 g) and Irgacure 184 (5 mg) were dissolved in dry dichloromethane (2 cm$^3$) and the solution. was spread evenly on a 18×25 cm glass plate. The solvent was evaporated off to leave a thin film. It was then irradiated with a Philips UVA sunlamp (75 w) for 10 minutes. The resultant cross-linked polymer was removed as strips (scalpel), washed in dichloromethane (50 cm$^3$) and thoroughly dried. Yield 0.1 g, 50%.

Ir vmax (KCl disc): 2940, 2864, 1780, 1650, 1428, 1170, 995, 951, 799, 743, 722, 620 cm$^{-1}$.

EXAMPLE 2

Step 1

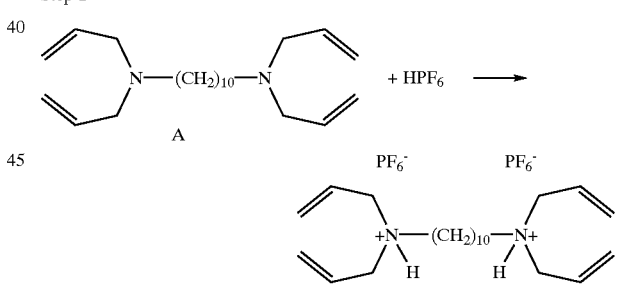

The monomer obtained in Example 1 step 1 (5.0 g) was treated with a 3M aqueous methanolic solution of hexafluorophosphoric acid (3.0 m) to pH1. The PF$_6^-$ salt was extracted using dichloromethane (2×100 cm$^3$) and the combined extracts were dried over MgSO$_4$. Removal of solvent left a yellow oil. 9.16 g, 96%.

Ir vmax (KCl disc): 3508, 3199, 2931, 2859, 2663, 1691, 1648, 1469, 427, 1290, 1142, 1049, 996, 953, 842.6 (s), 737 cm$^{-1}$.

$^1$HNMR (CDCL$_3$) δ: 1.25 (s, br, 12H), 1.65 (s, br, 4H), 2.95 (s, br, 4H), 3.65 (s, br, 8H), 5.60 (m, 8H), 5.90 (m, 4H), 9.75 (s, br, 2H).

Step 2

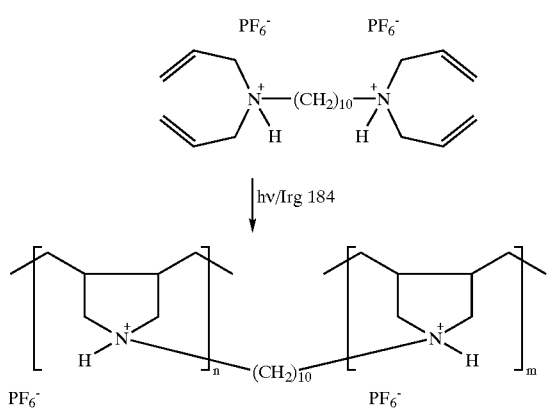

The monomer from step 1 (0.2 g) was dissolved with Irgacure 184 (5 mg) in dry dichloromethane (1.0 cm³) and the solution spread evenly on a 2×4 sq" sheet of aluminium. The solvent was removed by warming and the film was irradiated with the Philips UVA (75 w) u/v lamp for 10 minutes to form a cross-linked polymeric coating.

Ir vmax: 3434, 2937, 2859, 2717, 1674, 1467, 1297, 1140, 843 (s) (P-F), 558 cm$^{-1}$.

EXAMPLE 3

Step 1

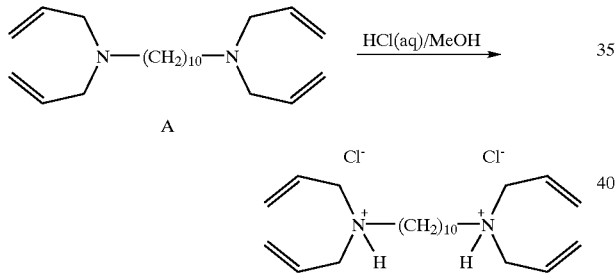

The monomer from Example 1 step 1 (1.0 g) was treated with 3M aqueous methanolic hydrochloric acid to pH 1.0 (universal indicator paper). The organic phase was extracted with dichloromethane (100 cm³) and washed with brine (60 cm³) then water (60 cm³) and dried over MgSO$_4$. Removal of solvent left a heavy yellow oil. 1.2 g, 96%.

Ir vmax (KCl. Disc): 2929, 2855, 2632, 2536, 1645, 1456, 1426, 1362, 1222, 997, 948 cm$^{-1}$.

$^1$HNMR (DMSO) δ: 1.25 (m, 10H), 1.67 (m, 4H), 2.89 (m, 4H), 3.66 (s, 8H), 5.42–5.53 (m, 8H), 5.96–6.01 (m, 4H), 11.20 (s, 2H).

Step 2

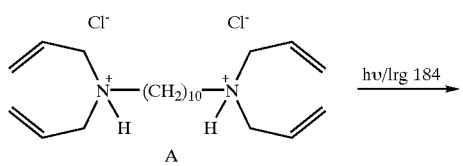

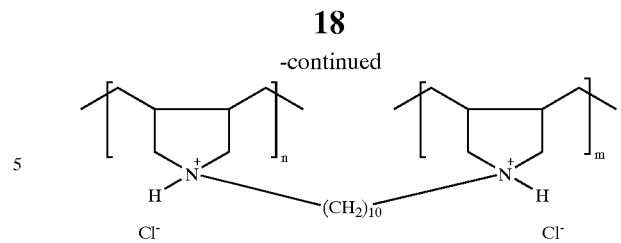

The diallylamine salt obtained in step 1 above (1.0 g, 0.0025 mol) and Irgacure 184 (25.3 mg, 0.000124 mol) were dissolved in dry dichloromethane (2 cm³) and the solution spread on an 18×25 cm² glass plate. The solvent was allowed to evaporate and the remaining clear film was irradiated for approximately 3 minutes under a Philips UVA (75 w) sunlamp. The resultant cross-linked polymer was removed from the glass plate, washed in dichloromethane and. Yield 0.75 g, 775%.

Ir vmax (KCl disc): 2800–2200 (broad), 1620 (w), 1455 (s), 1050 (w), 1000 (w), 950 (w), 720 (w) cm$^{-1}$.

EXAMPLE 4

Step 1

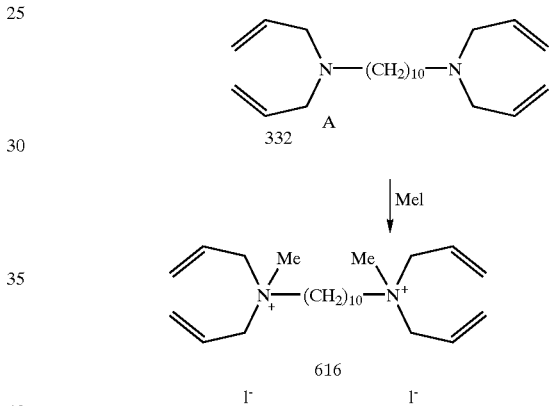

The monomer obtained as described in Example 1 step 1 (3.0 g, 0.0094 mol) and methyl iodide (2.60 g, 0.22 mol) in dry dichloromethane (30 cm³) were refluxed together for 7 hours. The solvent and residual methyl iodide were removed in vacuo and the orange residue re-dissolved in dry dichloromethane (100 cm³). The orange solution was washed in brine (50 cm³) and dried over MgSO$_4$. Removal of solvent gave an orange oil which formed a soft solid on standing. Yield 4.95 g, 89%.

$^1$HNMR (DMSO) δ: 1.27 (m, 12H), 1.69 (m, 4H), 2.99 (6H), 3.10–3.20 (m, 4H), 3.95 (d, 8H), 5.55–5.75 (m, 8H), 5.95–6.18 (m, 4H).

Ir vmax (KCl disc): 3081, 2925, 2854, 2361, 1689, 1641, 1470, 1424, 1371, 1302, 1246, 994, 943, 894, 868, 724, 6.68.

Step 1A

In an alternative preparation of the compound of step 1 above, the monomer obtained as described in Example 1 step 1 above (10.0 g, 0.030 mol) and methyl iodide (9.23 g, 0.065 mol) in a mixture of tetrahydrofuran (100 cm³) and dichloromethane (20 cm³) were stirred together. After 0.5 hour the solution began to become turbid and the turbidity increased as time progressed. The solvent was removed in vacuo and the white solid residue was suspended in 40/60 petrol (100 cm³) and stirred for 1 hour. Filtration and thorough drying in vacuo gave 17.79 g, 96% of a white, soft solid.

¹HNMR (CDCl₂) δ: 1.20–1.40 (s, 12H), 1.80 (s, 4H), 3.20 (s, 6H), 3.40 (m, 4H), 4.15 (m, 8H), 5.65–5.86 (m, 8H), 5.95–6.10 (m, 4H).

Ir νmax (KCl disc): 3080, 3050, 2930, 2860, 1640, 1470, 1440, 1425, 1370, 1300, 995, 945 cm⁻¹.

Step 2

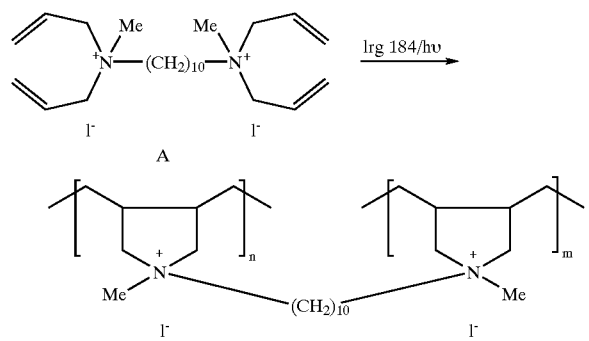

The monomer from step 1 above (0.7 g, 0.00114 mol) and Irgacure 184 (23.2 mg, 0.00014 mol) were dissolved in dry dichloromethane (3 cm³). The monomer/photoinitiator mixture was spread evenly on an 18×25 cm³ glass plate and the solvent left to evaporate in air to leave a clear, light yellow film. The film was irradiated with a Philips UVA (75 w) sunlamp for 15 minutes. Examination showed that the monomer had polymerised to form a hard, cross-linked polymer. The polymer was removed as strips of clear film and placed in dry dichloromethane (100 cm³) and the mixture stirred for 15 minutes. The film strips were removed by filtration and dried in vacuo.

Ir νmax (KCl disc): 2923, 2852, 1680 (w), 1613, 1461 (s), 950 (s), 726 cm⁻¹.

A similar reaction using 1.0 g(0.0016 mol) of the monomer obtained in step 1A above and 16.3 g (0.00008 mol) Irgacure 184 produced 0.84 g (84%) of cross-linked polymer.

Ir νmax (KCl disc): 3480 (H₂₀), 2920, 2860, 1640 (w), 1460, 1000, 955 cm⁻¹.

EXAMPLE 5

Step 1

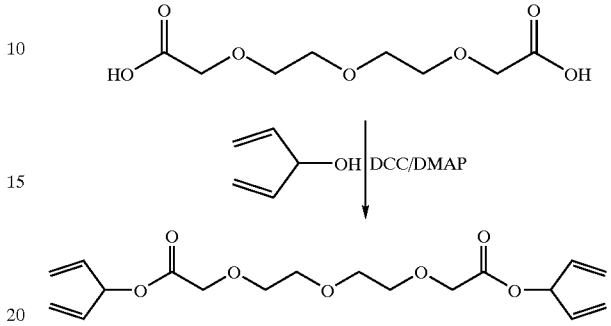

3,6,9-Trioxaundecandioic Acid (4.4 g, 0.0179 mol), 1,4-pentadien-3-ol (3.0 g, 0.0357 mol), 1,3-dicyclohexylcarbodiimide (7.63 g, 0.037 mol) and 4-dimethylaminopyridine (250 mg) were stirred together in dry dichloromethane (100 cm³) for 48 hours at room temperature. The 1,3-dicyclohexylurea was removed by filtration and the, solvent removed in vacuo to leave an oil. Purification using silica gel and ethyl acetate—40:60 petrol (1:1) as eluent followed by removal of solvent and thorough drying gave 6.4 g, 91% of colourless, clear oil.

Ir νmax (thin film): 2920, 2860, 1750, 1635, 1420, 1380, 1350, 1270, 1250, 1195, 1150, 1120, 990, 935, 880, 850, 730, 690, 580 cm⁻¹.

¹HNMR (CDCl₃) δ: 3.65–3.80 (m, 8H), 4.15 (s, 4H), 5.25–5.50 (m, 10H), 5.75–5.95 (m, 4H).

Step 2

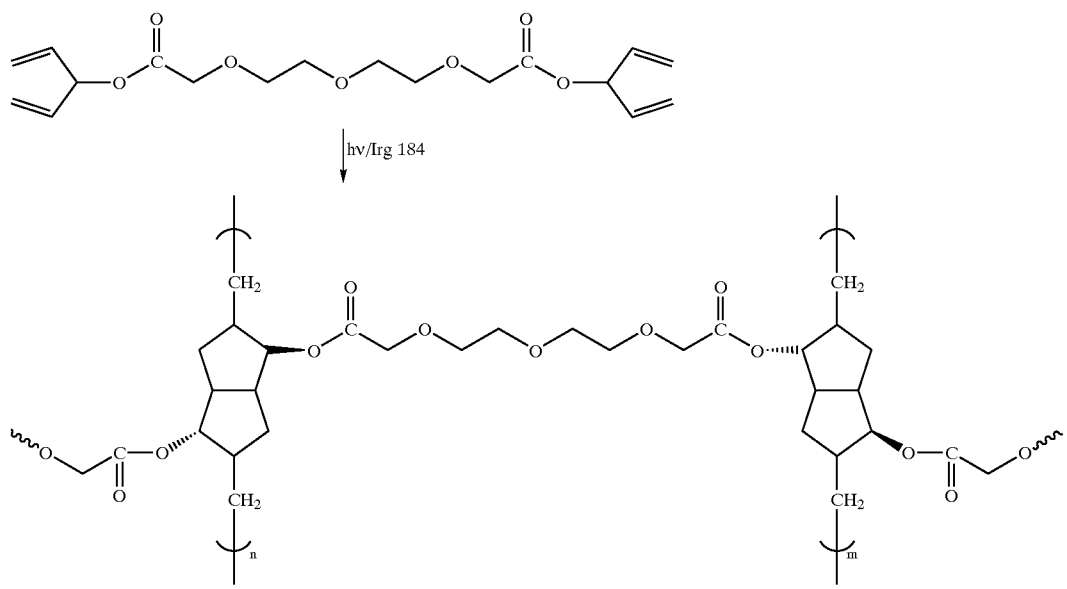

The monomer from Example 5 step 1 (1.5 g, 0.0042 mol) and Irgacure 184 (43 mg) were dissolved in dry dichloromethane (2 ml) and the solution was spread evenly on an 18×25 cm plate glass sheet. The solvent was allowed to dry in air then the remaining polymer/photoinitiator film was irradiated beneath a Philips UVA (70 w) U/V sunlamp for 2 hours. The resultant cross-linked polymer was scraped (scalpel) from the plate and suspended in dry dichloromethane (20 ml) and the suspension was stirred for approximately 15 minutes. The polymer was recovered by filtration and the retained solid washed with dry dichloromethane (2×16 cm³) and then dried thoroughly to leave 0.6 g 40% of clear film polymeric material.

Ir vmax (thin film): 2920, 2860, 1740, 1630, 1450, 1380, 1275, 1200, 1145, 1120, 850 cm⁻¹.

EXAMPLE 6

Step 1

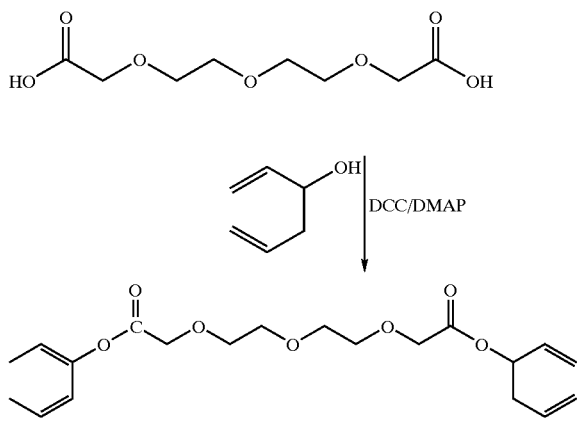

3,6,9-Trioxaundecandioic acid (5.33 g, 0.024 mol), 1,5-Hexadien-3-ol (5.0 g, 0.051 mol), 1,3-dicyclohexylcarbodiimide (10.5 g, 0.051 mol) and 4-dimethylaminopyridine (250 mg) were stirred together in dry dichloromethane (50 cm³) at room temperature for 6 hours. The 1,3-dicyclohexylurea was removed by filtration and the solvent removed in vacuo to leave a yellow oil which was purified by column chromatography using silica gel/ethyl acetate. Yield 8.0 g, 87%.

¹HNMR (CDCl₃) δ: 2.4 (t, 4H), 3.65 (m, 8H), 4.20 (s, 4H), 5.05–5.45 (m, 10H), 5.65–5.90 (m, 4H).

Ir vmax (thin film): 2920, 2860, 1760, 1640, 1425, 1200, 1150, 1120, 990, 920 cm⁻¹.

Step 2

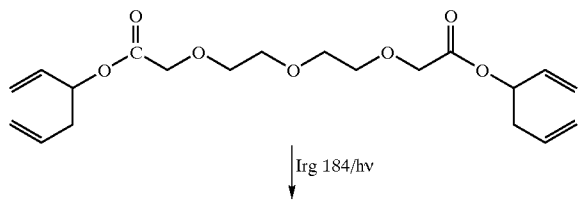

-continued

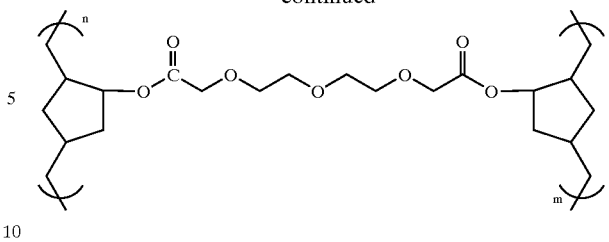

The monomer from step 1 above (1.6 g, 0.0042 mol) and Irgacure 184 (43 mg, 5 mol%) were dissolved in dry dichloromethane (2 ml) and the solution was spread evenly on an 18×25 cm plate glass sheet. The solvent was allowed to dry in air then the remaining polymer/photoinitiator film was irradiated beneath a Philips UVA (70 w) U/V sunlamp for 2 hours. The resultant cross-linked polymer was scraped (scalpel) from the plate land suspended in dry dichloromethane (20 ml) and the suspension was stirred for approximately 15 minutes. The polymer was recovered by filtration and the retained solid washed with dry dichloromethane (2×10 cm³) and then dried thoroughly to leave a clear film polymeric material. Yield 1.34 g, 87%.

Ir vmax (thin film): AWH/11: 2920, 2860, 1740 (S), 1635, 1450, 1430, 1380, 1280, 1200, 1145, 1120, 990, 925, 850 CM−1.

EXAMPLE 7

Step 1

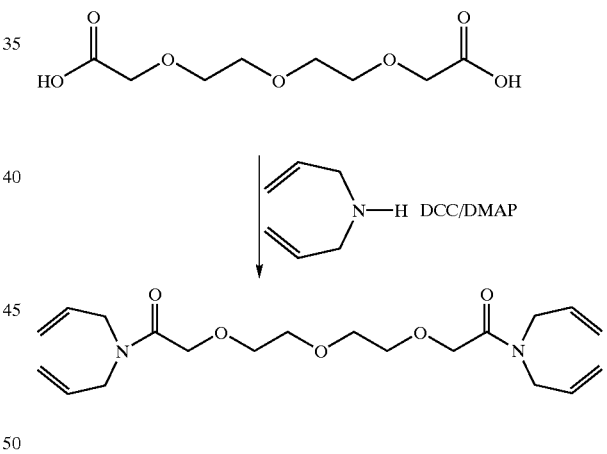

3,6,9-Trioxaundecanoic acid (5.0 g, 0.026 mol), diallylamine (5.10 g, 0.055 mol), 1,3-Dicyclohexylcarbodiimide (11.35 g, 0.055 mol) and 4-dimethylaminopyridine,(0.5 g) were stirred together in dry dichloromethane (100 cm³) for 6 hours. The resultant 1,3-dicyclohexylurea was removed by filtration and the solvent removed in vacuo to give a yellow oil. Column chromatography using ethyl acetate—petrol 40/60 (1:1) followed by removal of solvent in vacuo and thorough drying gave the product as a yellow oil. (Yield 8.0 g, 94%)

Ir vmax (thin film): 2930, 2860, 1660 (s), 1530, 1470, 1450, 142, 1350, 1280, 1230, 1195, 1115 (s), 995, 930, 755 cm⁻¹.

¹HNMR (CDCl₃) δ: 3.70 (m, 8H), 3.90 (m, 4H), 4.0 (m, 4H), 4.25 (s, 4H), 5.10–5.25 (m, 8H), 5.75–5.90 (m, 4H).

Step 2

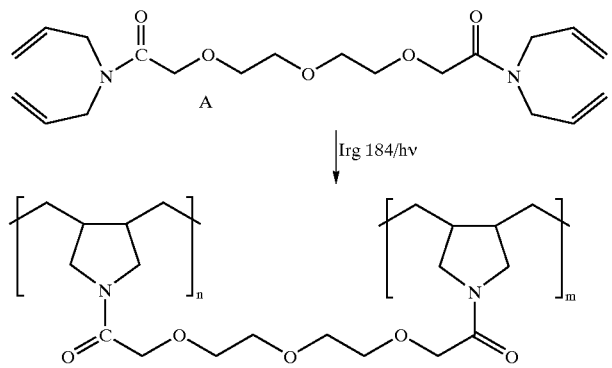

Monomer from step 1 above (1.0 g, 0.00263 mol) and 5 mol % Irgacure 184 (27 mg, 0.00013 mol) were dissolved in dry dichloromethane (3 cm³ and the solution spread over an 18×25 cm glass plate. The solvent was allowed to evaporate to leave a thin clear film. The film was then irradiated with a Philips UVA sunlamp (75 w) for approximately 5 minutes to form a hard polymeric cross-linked coating. The coating was removed and washed in dry dichloromethane and then thoroughly dried (Yield 0.73 g, 73%)

Ir $\nu_{max}$ (KCl disc): 2920, 2860, 1640 (s), 1530, 1450, 1240, 1115 (s), 730 cm$^{-1}$.

EXAMPLE 8

Step 1

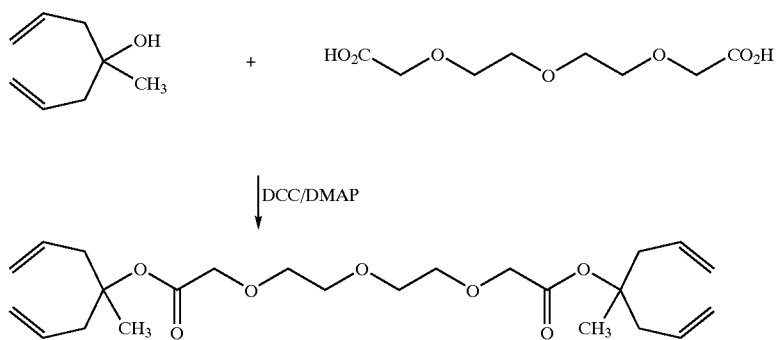

3,6,9-Trioxaundecandioic acid (2.64 g, 0.012 mol), 1,1-diallylethanol (3.0 g, 0.023 mol), 1,3-dicyclohexylcarbodiimide (5.16 g, 0.025 mol) and 4-dimethylaminopyridine (150 mg) were dissolved in dry dichloromethane (100 cm³) and the solution stirred for 18 h at room temperature. 1,3-Dicyclohexylurea was removed by filtration and the solvent removed in vacuo to leave a yellow oil. Column chromatography using silica gel and ethyl acetate gave, after removal of solvent in vacuo, a clear oil, 4.9 g, 94%.

$^1$HNMR (CDCl$_3$) δ: 1.45 (s, 8H), 2.50–2.70 (m, A:B, 8H), 3.70 (s, 6H), 4.05 (s, 4H), 5.05–5.15 (m, 8H), 5.70–5.90 (m, 4H).

Ir $\nu_{max}$ (thin film): 2920, 2870, 1750, 1450, 1380, 1210, 1150, 1120, 740, 700 cm$^{-1}$.

Step 2

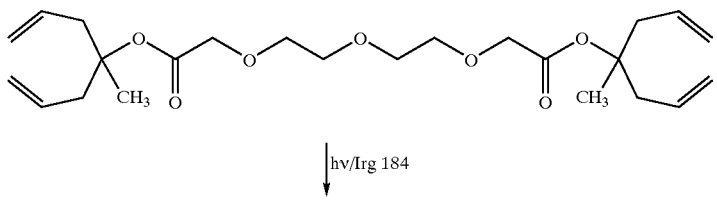

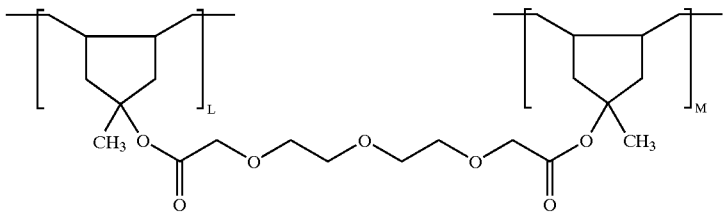

The monomer from Step 1 above (1.0 g, 0.0023 mol) and Irgacure 184 (5 mol %; 23.5 mg, 0.00012 mol) were dissolved in dry dichloromethane (3 cm$^3$) and the solution spread over a 18×25 cm glass plate. The solvent was allowed to evaporate to leave a thin clear film. The film was them irradiated with a Philips UVA sunlamp (75 w) to form a hard cross-linked polymer coating. The coating was removed and washed in dry dichloromethane and then dried thoroughly. Yield 0.78 g, 78%.

Ir vmax (KCl disc): 2940, 2880, 1750, 1450, 1380, 1205, 1145, 1120, 1030, 960 cm$^{-1}$.

EXAMPLE 9

Step 1

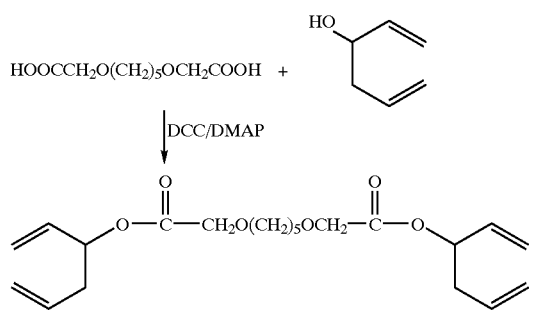

The diacid shown above (2.5 g, 0.0114 mol), 1,5-hexadien-3-ol (1.34 g, 0.024 mol), 1,3-dicyclohexylcarbodiimide (206.33) (5.16 g, 0.025 mol) and 4-dimethylaminopyridine (200 mg) were placed in dry dichloromethane (100 cm$^3$) and the solution stirred for 18 hours at room temperature. 1,3-dicyclohexylurea was removed by filtration and the solvent removed in vacuo to leave a yellow oil. Column chromatography using silica gel with ethyl acetate gave a clear oil, 2.84 g, 66%.

$^1$HNMR (CDCl$_3$) δ: 1.20 (quin, 2H), 1.65 (m 4H), 2.40 (t, 4H), 3.60 (d, 4H), 4.20 (s, 4H), 5.05–5.45 (m, 10H), 5.65–5.90 (m, 4H).

Ir vmax (thin film): 2920, 2860, 1750, 1700, 1510, 1430, 1240, 1200, 1140, 1030, 990, 920, 760 cm$^{-1}$.

Step 2

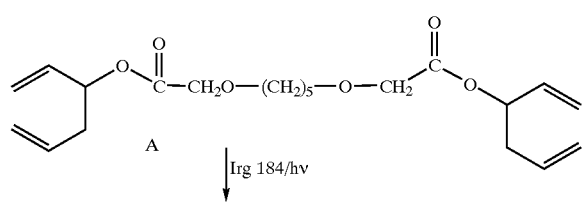

-continued

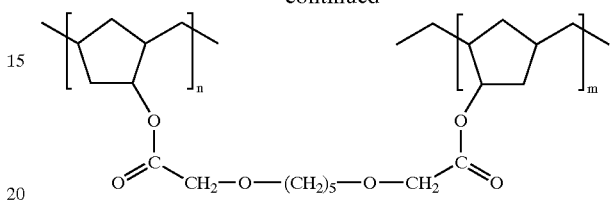

Monomer from step 1 above (0.7 g, 0.001894 mol) and Irgacure 184 (37.6 mg, 0.0000184 mol) were dissolved in dry dichloromethane (3 cm$^3$) and the solution was spread on an 18×25 cm$^3$ glass plate. The solvent was allowed to evaporate to leave a clear film. This was irradiated with a Philips UVA (75 w) sunlamp for 2 hours until the film hardened. The film was removed and placed in dry dichloromethane (50 cm$^3$) and stirred for 1 hour. The cross-linked polymer was removed by filtration and washed with dry dichloromethane (2×50 cm$^3$) and dried thoroughly to leave a creamy coloured polymeric solid. Yield 0.35 g, 50%.

Ir vmax (KCl disc) 2940, 2860, 1750 (s), 1450, 1285, 1205, 1130, 1030 cm$^{-1}$.

EXAMPLE 10

Step 1

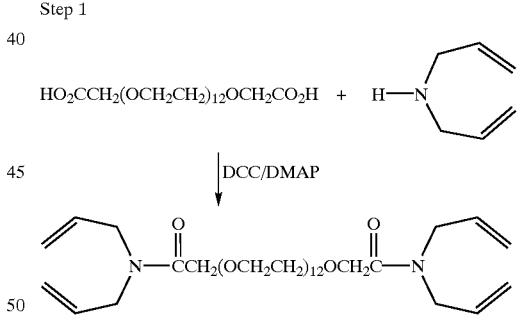

Polyethylene glycol 600 diacid (12.0 g, 0.020 mol), diallylamine (4.67 g, 0.048 mol), 1,3-dicyclohexylcarbodiimide (10.6 g, 0.048 mol) and 4-dimethylaminopyridine (600 mg) were placed in dichloromethane (100 cm$^3$) and the mixture stirred for 24 hours at room temperature. The 1,3-dicyclohexylurea was removed by filtration and the solvent removed in vacuo to leave a yellow oil. Column chromatography (silica gel/ethyl acetate) followed by removal of solvent in vacuo gave a pale yellow oil. 13.90 g, 92%.

$^1$HNMR (CDCl$_3$) δ: 3.60 (m, 48H), 3.90 (d, 4H), 4.0 (d, 4H), 4.20 (s, 4H), 5.15 (m, 8H), 5.75 (m, 4H).

Ir vmax (thin film): 3016, 2922, 1662 (s), 1470, 1353, 1219, 1114, 931, 756, 666 cm$^{-1}$.

Step 2

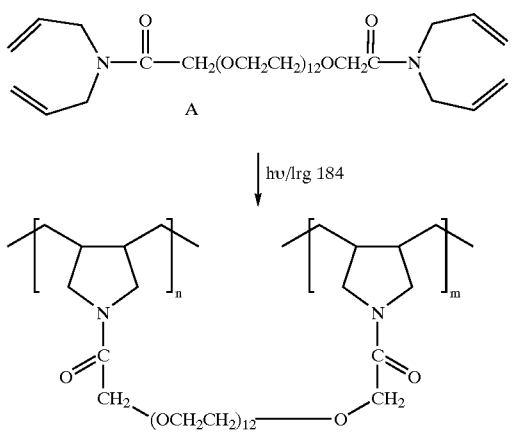

Monomer from Step 1 (1.0 g) and Irgacure (1.5 mg) were dissolved in dry dichloromethane (3 cm$^3$) and thoroughly mixed. The solution was spread evenly on an 18×25 cm glass plate and the solvent allowed to evaporate to leave a thin film of monomer. The film was irradiated with the Philips UVA (75 w) sunlamp for 30 minutes to form a soft, permeable to water, cross-linked polymer film.

Ir vmax (thin film): 3438, 2946, 2371, 1703, 1648 (s), 1544, 1510, 1457, 1352, 1099 (vs), 953, 856, 727, 551 cm$^{-1}$.

EXAMPLE 11

Step 1

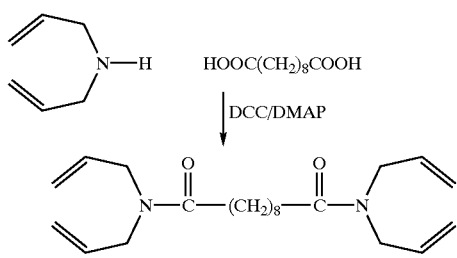

Diallylamine (9.72 g, 0.1 mol), Sebacic acid (10.00 g, 0.0050 mol), 1,3-dicyclohexylcarbodiimide (22.70 g. 0.11 mol) and 4-dimethylaminopyridine (0.450 g) were stirred together in dry dichloromethane (100 cm$^3$) for 6 hours. The resultant 1,3-dicyclohexylurea was removed by filtration and the solvent removed in vacuo to give a yellow oil. Column chromatography using ethyl acetate—petrol 40/60 (1:1) followed by removal of solvent in vacuo and thorough drying gave the product as a yellow oil. 15.90 g, 90%.

Ir vmax (thin film): 2920, 2850, 1690 (w), 1640 (s), 1520, 1460, 1410, 1220, 990, 920, 730 cm$^{-1}$.

$^1$HNMR (CDCl$_3$) δ: 1.10–1.45 (m, 6H), 1.50–2.00 (m, 6H), 2.40 (t, 4H), 3.90 (d, 4H), 4.0 (d, 4H), 5.05–5.20 (m, 8H), 5.20–5.90 (m, 4H).

Step 2

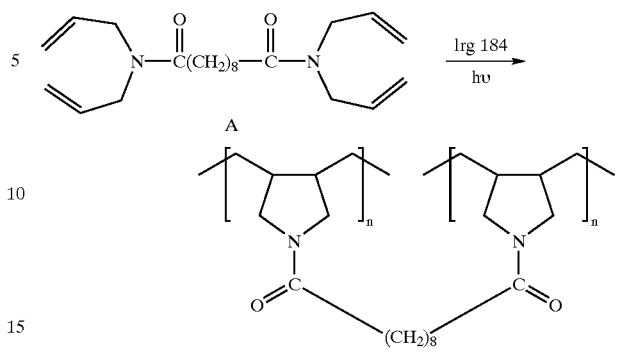

Monomer from Step 1 (1.00 g, 0.0028 mol) and Irgacure 184 (28.3 mg, 0.000139 mol) were dissolved in dry dichloromethane (3 cm$^3$) and the solution spread over a 18×25 cm glass plate. The solvent was allowed to evaporate to leave a thin clear film. The film was then irradiated with a Philips UVA sunlamp (75 w) for approximately 5 minutes to form a hard polymeric cross-linked coating. The coating was removed and washed in dry dichloromethane and then thoroughly dried.

Yield 0.80 g, 80%. Ir vmax KCl disc): 2920, 2860, 1640, 1530, 1450, 1230 (w), 1340 (w), 1230 (w), 1000 (w), 930 (w).

EXAMPLE 12

Step 1

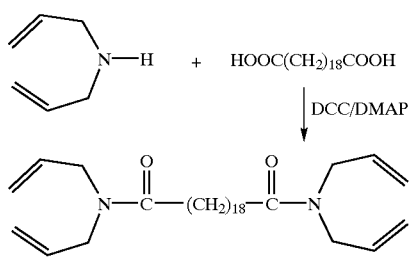

Eicosanedioic acid (5.0 g, 0.0146 mol), diallylamine (3.12 g, 0.032 mol), 1,3-dicyclohexylcarbodiimide (6.60 g, 0.032 mol) and 4-dimethylaminopyridine (200 mg) were dissolved in dichloromethane/tetrahydrofuran mixture (1:1) (100 cm$^3$) and the mixture stirred at room temperature for 72 hours. 1,3-Dicyclohexylurea was removed by filtration and the solvent removed in vacuo to leave a yellow oil. Column chromatography using silica gel/ethyl acetate followed by removal of solvent in vacuo and thorough drying gave a pale yellow oil. 6.35 g, 87%.

$^1$HNMR (CDCl$_3$) δ: 1.20 (s, br, 28H), 1.60 (m, 4H), 1.80 (m, 4H), 3.90 (d, 4H), 4.0 (d, 4H), 5.10 (m, BH), 5.75 (m, 4H).

Ir vmax (thin film): 3006, 2927, 2854, 1643, 1530, 1466, 1415, 1217, 1084, 992,. 925, 893, 756, 666 cm$^{-1}$.

Step 2

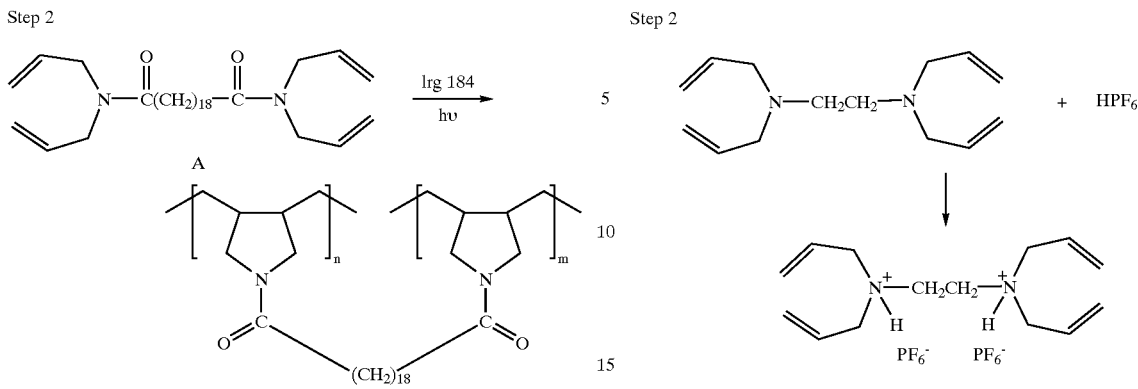

Monomer from Step 1 (0.25 g) and Irgacure 184 (5 mg) were dissolved in dry dichloromethane (1.0 cm³) and the solution was heated (water bath) to ensure even distribution of photoinitiator. The solution was spread evenly on a 4×2" piece of aluminium foil and the solvent was allowed to evaporate off to leave a thin film of monomer/photoinitiator. This was irradiated with a Philips UVA (75 w) sunlamp for 30 minutes until a hard cross-linked polymer was formed. To test for hydrophobicity, the foil+polymer was subjected to running water for 30 minutes. After this time the polymer laminate was not adversely affected, i.e. no loss of adhesion to the foil.

Ir νmax (KCl disc): 2924, 2851, 1648, 1534, 1452, 1227, 721 cm$^{-1}$.

EXAMPLE 13

Step 1

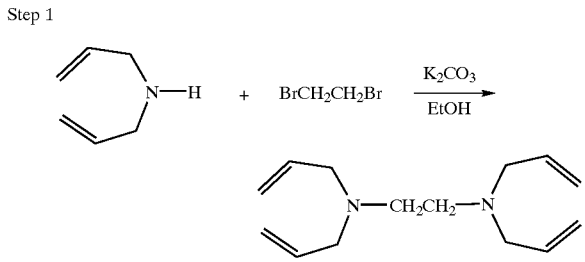

Diallylamine (12.90 g, 0.132 mol), 1,2-dibromoethane (12.40 g, 0.066 mol) and potassium carbonate (18.80 g, 0.132 mol) were refluxed in ethanol (100 cm³) for 24 hours. Solids were removed by filtration and solvents removed in vacuo to leave a yellow oil. The oil was purified by column chromatography (silica gel/ethyl acetate) to leave a pale yellow oil. 13.40, 92%.

$^1$HNMR (CDCl$_3$) δ: 2.55 (s, 4H), 3.10 (d, 8H), 5.10 (m, 8H), 5.80 (m, 4H).

Ir νmax (thin film): 3082, 3012, 2983, 2927, 2806, 1645, 1447, 1420, 1355, 1262, 1109, 997, 919, 559 cm$^{-1}$.

Step 2

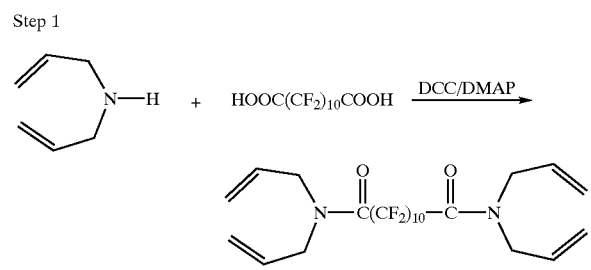

Monomer from Step 1 (5.0 g) was treated with an aqueous methanolic solution of hexafluorophosphonic acid 60% solution in H$_2$O (3.0 m) to pH1. The PF$_6^-$ salt was extracted using dichloromethane (2×100 cm³) and the combined extracts were dried over MgSO$_4$. Removal of solvent left a yellow oil. 8.0 g, 96%.

$^1$HNMR (CDCl$_3$) δ: 3.60 (d, 2H), 3.75 (d, 2H), 3.80 (s, 8H), 5.55 (m, 8H), 5.90 (m, 4H), 9.80 (s, br, 2H).

Ir νmax (thin film): 3428, 2986, 2634, 1460, 1426, 1294, 1246, 1142, 1053, 977, 953, 842, 740 cm$^{-1}$.

The product may then be polymerised, for example as described in Example 1 Step 3 above.

EXAMPLE 14

Step 1

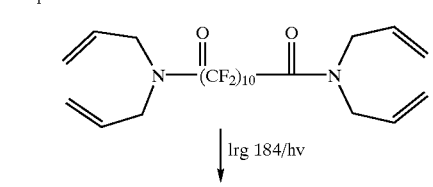

Diallylamine (1.41 g, 0.0145 mol), perfluoro-1,10-decanedicarboxylic acid (2.5 g, 0.0073 mol), 1,3-dicyclohexylcarbodiimide (3.20 g, 0.0155 mol) and 4-dimethylaminopyridine (0.5 g) were stirred together in dry dichloromethane (60 cm³) for 6 hours. The solvent was removed in vacuo to leave a white solid which was purified using column chromatography (ethyl acetate-petrol 40/60 1:1) and dried thoroughly to give 2.96 g, 79% of clear oil.

$^1$HNMR (CDCl$_3$) δ: 3.90 (d, 4H), 4.00 (d, 4H), 5.10–5.25 (m, 8H), 5.70–5.81 (m, 4H).

Ir νmax (thin film): 2933, 2857, 1692, 1645.5, 1611.4, 1576, 1454, 1419, 1377, 1350, 1219, 1151, 1081, 992, 932, 892, 735, 657, 556.

Step 2

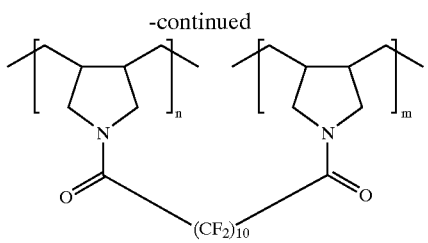

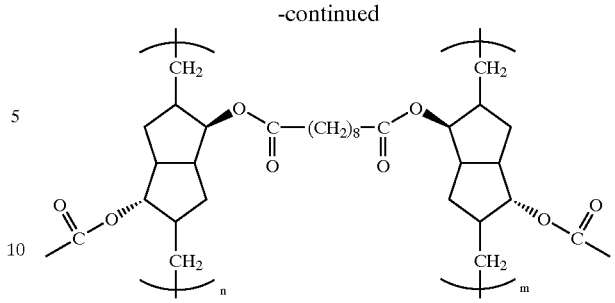

Monomer from Step 1 (1.0 g, 0.0019 mol) was dissolved in dry dichloromethane (3 cm³) and Irgacure 184 (20 mg, 0.000095 mol) and the resultant solution spread evenly over an 18×25 cm glass plate. The solvent was allowed to evaporate off to leave a clear liquid layer of monomer/photoinitiator. The plate was placed under a Philips UVA (75 w) sunlamp for approximately 15 minutes. The resultant clear film was removed (powdery) and dried after stirring for 30 minutes in dry dichloromethane (100 cm³) to leave 0.79 g, 79% of white powder.

Ir vmax (thin film): 2936, 2859, 1691, 1624, 1576, 1455, 1372, 1218, 1151, 1079, 892, 729, 654, 555 cm$^{-1}$.

EXAMPLE 15

Step 1

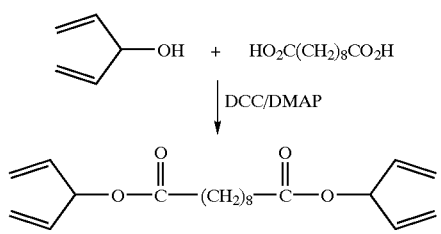

Sebacic acid (2.0 g, 0.0099 mol), 1,4-pentan-3-ol (1.7 g, 0.02 mol), 1,3-dicyclohexylcarbodiimide (4.52 g, 0.022 mol) and 4-dimethylaminopyridine (200 g) in dry dichloromethane (60 cm³) were stirred together for 18 hours. The 1,3-dicyclohexylurea was removed by filtration and solvent removed to leave clear oil. This was dissolved in 40/60 petrol (100 cm³) and washed in water then dried over MgSO$_4$. Removal of solvent left a clear, colourless oil which tlc (dichloromethane) (developing in iodine) showed as a single spot. The oil was thoroughly dried it vacuo to leave 2.49 g, 75% of clear oil.

$^1$HNMR (CDCl$_3$) δ: 1.30 (s, 8H), 1.60 (t, 4H), 2.35 (t, 4H), 5.15–5.35 (m, 8H), 5.65–5.95 (m, 6H).

Ir vmax (thin film): 2920, 2860, 1730, 1640, 1510, 1460, 1410, 1365, 1240, 1165, 1095, 985, 930 cm$^{-1}$.

Step 2

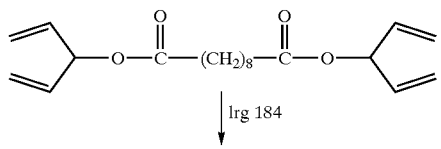

| Irg 184

Monomer from Step 1 (1.0 g, 0.003 mol) and Irgacure 184 (31 mg, 0.00015 mol) were dissolved in dry dichloromethane (2 ml) and the solution was spread evenly on an 18×25 cm plate glass sheet. The solvent was allowed to dry in air then the remaining polymer/photoinitiator film was irradiated beneath a Philips UVA (75 w) sunlamp for 2 hours. The resultant cross-lnked polymer was scraped (scalpel) from the plate and suspended in dry dichloromethane (20 ml) and the suspension was stirred for approximately 15 minutes. The polymer was recovered by filtration and the retained solid washed with dry dichloromethane (2×10 cm³) and then dried thoroughly to leave 0.85 of clear film polymeric material.

Yield 0.85 g, 85%.

Ir vmax (thin film): 2920, 2860, 1725, 1520, 1450, 1365, 1240, 1170, 1090, 985 cm$^{-1}$.

EXAMPLE 16

Step 1

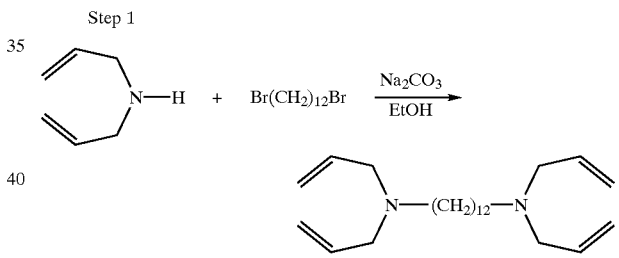

Diallylamine (12.70 g, 0.134 mol), 1,12-dibromododecane (20.0 g, 0.061 mol) and potassium carbonate (18.50 g, 0.134 mol) in ethanol (100 cm³) were refluxed together for 18 hours. The solids were removed by filtration and the solvent removed in vacuo to leave a yellow oil. The oil was passed through a silica gel column using ethyl acetate as the eluent. Removal of solvent in vacuo gave a pale yellow oil which was thoroughly dried. Yield 17.4 g, 79%.

$^1$HNMR (CDCl$^3$) δ: 1.20 (m, 16H), 1.45 (t, 4H), 2.40 (t, 4H), 3.10 (d, 8H), 5.05–5.15 (m, 8H), 5.80 (m, 4H).

Ir vmax (thin film): 3080, 3020, 2920, 2860, 2800, 1645, 1470, 1420, 1355, 1260, 1155, 1115, 1090, 1000, 920, 725 cm$^{-1}$.

Step 2

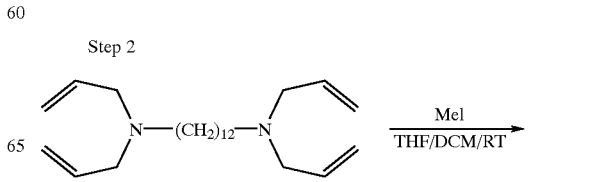

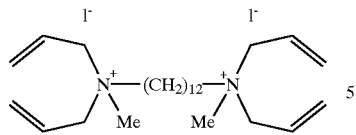

The diamine from step 1 (10.00 g, 0.028 mol) and methyl iodide (8.52 g, 0.060 mol) in a mixture of tetrahydrofuran (100 cm$^3$) and dichloromethane (20 cm$^3$) were stirred together. After 0.5 hours the solution began to become turbid and the turbidity increased as time progressed. The solvent was removed in vacuo and the white solid residue was suspended in 40/60 petrol (100 cm$^3$) and stirred for 1 hour. Filtration and thorough drying in vacuo gave 17.40 g, 97% of white, soft solid.

$^1$HNMR (CD$_2$Cl$_2$) δ: 1.15–1.40 (m, 16H), 1.80 (s, br, 4H), 3.20 (s, 6H), 3.30–3.45 (m, 4H), 4.15 (d, 8H), 5.65–5.90 (m, 8H), 5.95–6.15 (m, 4H).

Ir νmax (thin film): 2920, 2860, 1690, 1640, 1470, 1370, 1300, 1250, 1000, 945 cm$^{-1}$.

This material could be polymerised as described in previous examples.

EXAMPLE 17

Step 1

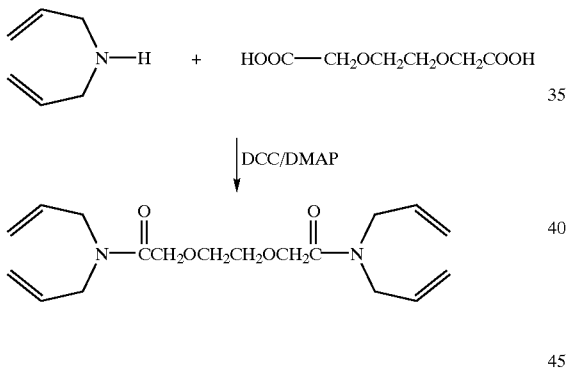

Diallylamine (8.80 g, 0.0090 mol), 3,6-dioxaoctandioic acid (8.00 g, 0.0448 mol) were mixed together as shown in Example 15 Step 1. The mixture was stirred in dichloromethane for 24 hours. The crude product was recovered and purified via silica gel/ethyl acetate to leave a clear oil. Yield 13.43 g, 89%.

$^1$HNMR (CDCl$_3$) δ: 3.70 (s, 4H), 3.80 (d, 4H), 3.95 (d, 4H), 4.20 (s, 4H), 5.20 (m, 8H), 5.60 (m, 4H).

Ir νmax (thin film): 3080, 2940, 2860, 1650, 1530, 1470, 1420, 1350, 1280, 1235, 1120, 995, 930, 860, 815 cm$^{-1}$.

Step 2

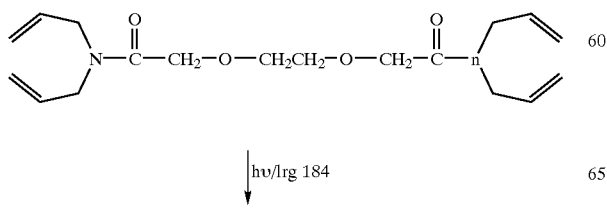

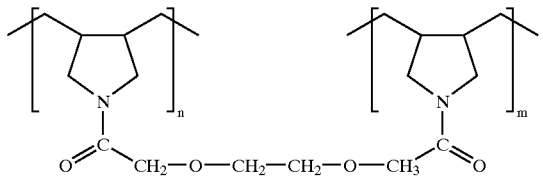

Irgacure 184 (5 mg) as placed in Monomer from Step 1 (0.2 g) and heated to form a clear solution. It was then stirred to ensure complete mixing of photoinitiator then placed on a 1.5 in$^2$ piece of copper (ex DRA) and spread evenly using 100 μm K bar. It was then irradiated for 1 hour beneath a Philips UVA sunlamp and allowed to stand for 24 hours.

Ir νmax (thin film): 2940, 2860, 1640 (strong), 1460, 1345, 1125, 730 cm$^{-1}$.

EXAMPLE 18

Step 1

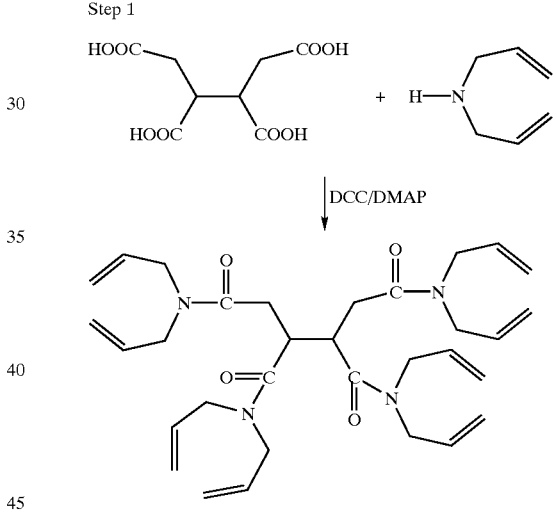

Meso-butan-1,2,3,4-tetracarboxylic acid (20.0 g, 0.0428 mol), diallylamine (39.0 g, 0.20 mol), 1,3-dicyclohexylcarbodiimide(82.50 g, 0.20 mol) and 4-dimethylaminopyridine (2.0 mg) were dissolved in dichloromethane/tetrahydrofuran (1:1) mixture (200 cm$^3$) and the mixture was stirred at room temperature for 120 hours. 1,3-dicyclohexylurea was removed by filtration and the solvent removed in vacuo to leave a yellow oil. Column chromatography (silica gel/ethyl acetate) followed by removal of solvent in vacuo gave a heavy pale yellow oil which solidified on standing. 42.3 g, 89%.

$^1$HNMR (CDCl$_3$) δ: 2.90 (m, 4H), 3.50 (m, 2H), 3.80 (m, 16H), 5.20 (m, 16H), 5.70 (m, 8H).

Ir νmax (thin film): 3323, 3086, 2935, 2861, 1650, 1545, 1416, 1363, 1228, 1135, 994, 925, 556 cm$^{-1}$.

Step 2

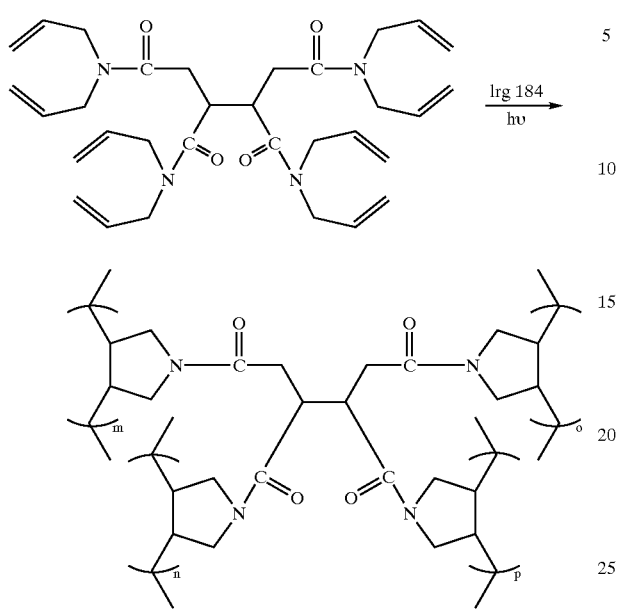

Monomer from Step 1 (1.0 g) was dissolved in dry dichloromethane (3 cm³). The Irgacure 184 (10 mg) was added to the solution, heated and mixed to ensure homogenicity. It was then spread evenly on an 18×25 cm glass plate and the solvent allowed to evaporate off to leave a thin, clear film. This was irradiated with a Philips UVA sunlamp for 30 minutes to form a hard cross-linked polymer film. This was removed (scalpel), washed in dichloromethane and dried. Yield 0.64 g, 64%.

Ir vmax (thin film): 3424, 2936, 2374, 2346, 1705, 1644 (s), 1524, 1436 (s), 1222, 1138, 992, 924, 561 cm$^{-1}$.

EXAMPLE 19

Step 1

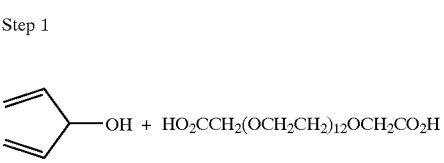

Polyethylene glycol 600 diacid (6.0 g, 0.010 mol), 1,4-pentadiene-3-ol (2.0 g, 0.024 mol), 1,3-Dicyclohexylcarbodiimide (206.33) (4.95 g, 0.024 mol) and 4-dimethylaminopyridine (300 mg) were stirred together in dry dichloromethane (50 ml) for 72 h. The resultant 1,3-Dicyclohexyl-urea was removed by filtration and removal of solvent left a clear oil. Column chromatography using silica gel and dichloromethane—40/60 petrol (1:1) followed by dichloromethane-methanol (1:3) gave, after removal of solvent, a colourless, clear oil. 6.73 g, 85%.

$^1$HNMR (CDCl$_3$) δ: 3.55–3.80 (m, 48H), 4.15 (s, 4H), 5.25–5.50 (m, 10H), 5.75–5.95 (m, 4H).

Ir vmax (thin film): 2860, 1745, 1635, 1450, 1345, 1250, 1195, 1140, 1115, 990, 940, 750 cm$^{-1}$.

Step 2

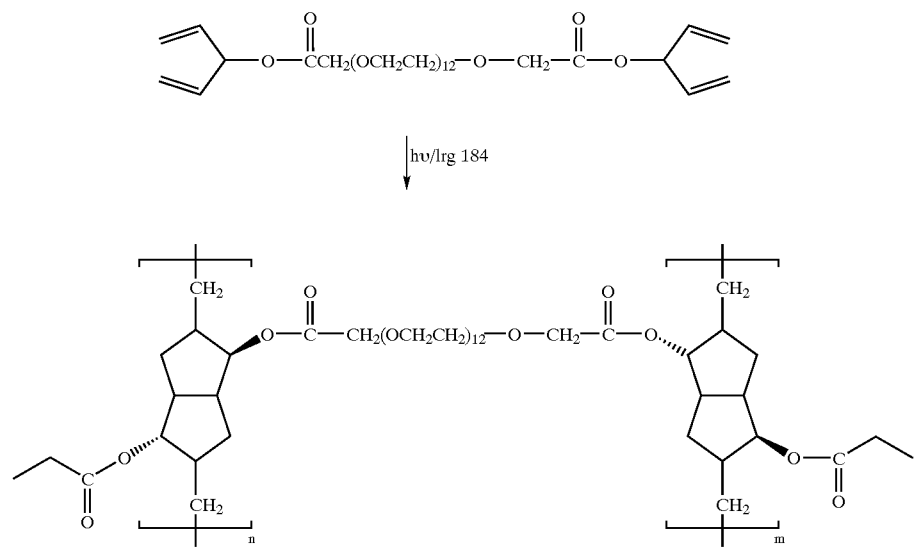

Monomer from Step 1 (1.60g, 0.0021 mol) and Irgacure 184 (21 mg, 0.000105 mol) were dissolved in dry dichloromethane (3 cm³) and the solution was spread over a 18×25 cm glass plate. The solvent was allowed to evaporate to leave a thin, clear film. The film was then irradiated with a Philips UVA sunlamp (75 w) to form a hard cross-linked polymer coating. The coating was removed and, washed in dry dichloromethane and dried thoroughly.

Yield 1.10 g, 67%.

Ir vmax (KCl disc): 2920, 2860, 1745, 1680, 1640, 1450, 1345, 1280, 1250, 1200, 1140, 1110, 950, 850 cm⁻¹.

EXAMPLE 20

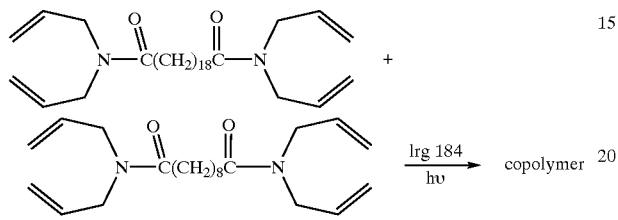

The Monomer of Example 12 Step 1 (0.5 g) and the monomer of Example 11 Step 1, were dissolved with the Irgacure 184 (20 mg) in dichloromethane (5 cm³) and the solution was spread evenly on an 18×25 cm glass plate. The solvent was evaporated off and the residual film irradiated with the Philips UVA (75 w) sunlamp for 1 hour. The resultant cross-linked copolymeric film was removed in strips (scalpel) and washed in dichloromethane, then thoroughly dried. The resultant film was soft, stretchy but of low tensile strength.

Ir vmax (thin film): 3431, 2931, 2858, 1649 (s), 1453, 720 cm⁻¹.

EXAMPLE 21

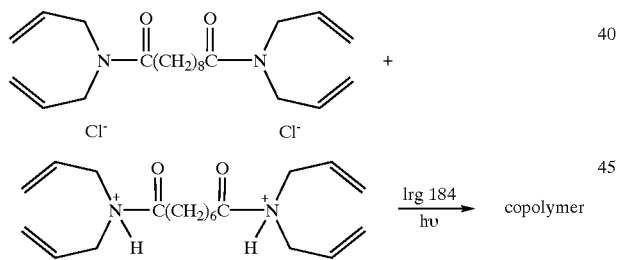

The monomer of Example 11 Step 2 (0.5 g) and monomer B above (0.5 g) (prepared by analgous methods to those described above) were dissolved in dry dichloromethane (5 cm³). The Irgacure 184 (20 mg) was added and the mixture warmed (water bath) until the photoinitiator had dissolved. The solution was spread evenly on an 18×25 cm glass plate and the solvent allowed to evaporate. The two monomers phase separated to give an even 'pimpled' effect. Attempts to mix the two monomers using dichloromethane and mechanical mixing resulted, after evaporation of solvent, in the same pimpled effect. The monomers were irradiated with the Philips UVA (75 w) sunlamp for 1 hour to form a phase-separated cross-linked solid polymeric 'pimpled' film but unstable due to the discontinuity of polymerisation at each phase boundary.

Ir vmax (thin film): 3421 (s), 2939 (s9), 1642 (s), 1456, 1167, 577 cm⁻¹.

EXAMPLE 22

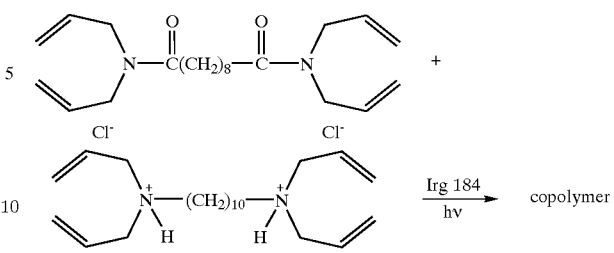

The monomer of Example 11 step 1 (0.5 g) and the monomer of Example 3 Step 2 (0.5 g), were dissolved with the Irgacure 184 (20 mg) in dichloromethane (5 cm³) and the solution was evenly spread on an 18×25 cm glass plate. The solvent was evaporated off to leave a residual clear film which was irradiated with the Philips UVA (75 w) sunlamp for 1 hour. The resultant cross-linked copolymer was removed in strips (scalpel) and washed in dichloromethane (50 cm³) then thoroughly dried.

Ir vmax (thin film): 3448 (s), 2931, 2855, 1629 (s), 1534, 1452, 1230, 731 cm⁻¹.

EXAMPLE 23

Other polymerisable monomers were produced as follows:

EXAMPLE 23a

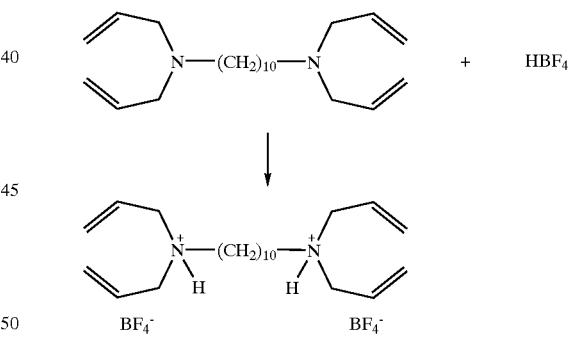

The monomer illustrated (5.0 g) above was treated with a 50% aqueous solution of fluoroboric acid to pH 1.0 (universal indicator paper). The organic phase was extracted using dichloromethane (2×75 cm³) and then dried over MgSO₄Removal of solvent in vacuo gave a heavy pale yellow oil. 7.40 g, 97%.

¹HNMR (CDCl₃) δ: 1.20 (s, br, 12H), 1.65 (s, br, 4H), 3.05 (quin, 4H), 3.75 (t, 8H), 5.55 (m, 8H), 5.90 (m,4H), 7.15 (s, br, 2H).

Ir vmax (thin film): 3410 (br), 2930, 2857, 2649, 1707, 1646, 1460, 1428, 1056.8 (very strong), 952, 763 cm⁻¹.

EXAMPLE 23b

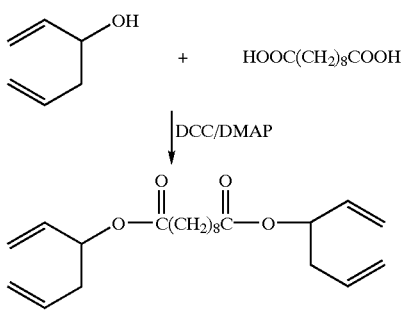

Using the procedure described in Example 23a, sebacic acid 10.06 g, 0.050 mol), 1,5-Hexadiene-3-ol (9.80 g, 0.1 mol), 1,3-dicyclohexylcarbodiimide (22.70 g, 0.11 mol) and 4-dimethylaminopyridine (450 mg) were mixed together to give the desired product.

Yield: 15.6 g, 87%; $^1$HNMR (CDCl$_3$) δ: 1.30 (s, 10H), 1.60 (t, 8H), 2.35 (s, 2H), 5.05–5.45 (m, 10H), 5.65–5.90 (m, 4H).

Ir vmax (thin film): 2920, 2860, 1730, 1640, 1510, 1460, 1410, 1365, 1235, 1160, 1095 cm$^{-1}$.

EXAMPLE 24

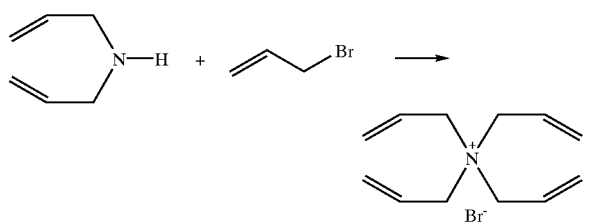

Diallylamine (10.09, 0.103 mol), allyl bromide (25.41 g, 0.21 mol) and potassium carbonate (20 g) were refluxed in ethanol. Solids were removed by filtration and the solvents were removed in vacuo to leave a yellow oil.

This compound could be used as a u.v curable adhesive.

EXAMPLE 25

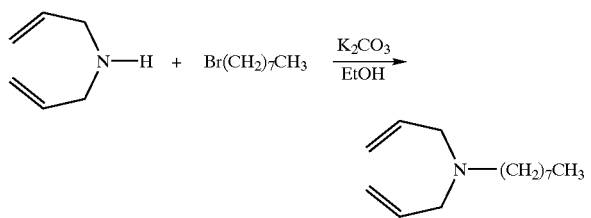

1-Bromooctane (15.0 g, 0.078 mol), diallylamine (8.26 g, 0.085 mol) and potassium carbonate (11.75 g, 0.085 mol) were refluxed in ethanol (100 cm$^3$) for 18 hours. Solids were removed by filtration and the solvents were removed in vacuo to leave a yellow oil. Column chromatography (silica gel/dichloromethane) followed by removal of solvent in vacuo and thorough drying gave 12.9 g, 79% of light yellow oil.

$^1$HNMR (CDCl$_3$) δ: 0.85 (t, 3H), 1.80 (s, br, 10H), 1.45 (s, br, 2H), 2.40 (5, 2H), 3.15 (d, 4H), 5.10 (m, 4H), 5.85 (m, 2H).

Ir vmax (thin film): 3082, 2932, 2860, 2806, 2355 (w), 1751 (w), 1709 (w), 1644 (m), 1463, 1419, 1379, 1262, 1083, 996, 919, 613 cm$^{-1}$.

EXAMPLE 26

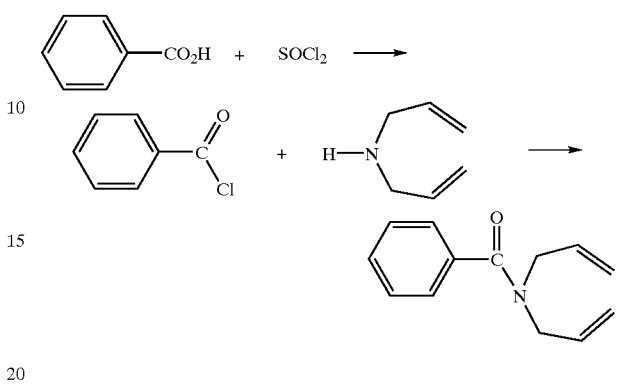

Benzoic acid (20.0 g, 0.164 mol) was placed in thionyl chloride (23.80 g, 0.20 mol) and the mixture heated to approximately 80° C. with stirring for 3 hours. Excess thionyl chloride was removed in vacuo and the residue cooled to approximately −5° C. in a salt/ice bath. Diallylamine (19.50 g, 0.20 mol) in dry dichloromethane (20 cm$^3$) was added dropwise with much evolution of HCl gas. After complete addition, the resultant brown solution was allowed to rise to room temperature and left stirring for one hour. It was then washed with 3N HCl (150 cm$^3$), saturated K$_2$CO$_3$ solution (150 cm$^3$) and brine (150 cm$^3$), then finally dried over MgSO$_4$. Removal of solvent gave a brown oil which was passed through a silica gel column using ethyl acetate as the eluent. Removal of solvent in vacuo gave a yellow oil. 27.10 g, 82%.

$^1$HNMR (CDCl$_3$) δ: 3.90 (s, br, 2H), 4.10 (s, br, 2H), 5.20 (m, 4H), 5.70 (s, br, 1H), 5.85 (s, br, 1H), 7.40 (m, 5H).

Ir vmax (thin film): 3087, 1640, 1498, 1456, 1413, 1262, 1120, 991, 928, 788, 703 cm$^{-1}$.

EXAMPLE 27

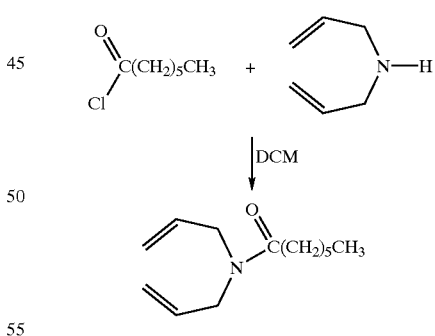

Heptanoyl chloride (25.0 g, 0.168 mol) was placed in dry dichloromethane (100 cm$^3$) and the solution cooled to −5° C. in a salt-ice bath. Diallylamine (17.5 g, 0.18 mol) in dry dichloromethane (25 cm$^3$) was added dropwise with much evolution of HCl gas. The resultant solution was allowed to rise to room temperature then poured into 3N HCl (300 cm$^3$) and stirred vigorously for ten minutes. The organic layer was removed by separation and to the aqueous layer was added ammonium chloride. This was then re-extracted with dichloromethane (2×100 cm$^3$) and the three organic extracts combined and dried over MgSO$_4$. Removal of solvent in vacuo left a brown oil (one spot on tlc—silica gel/ethyl acetate) which was passed through a silica gel column using ethyl acetate as the eluent. Removal of solvent in vacuo gave a yellow oil. 32.0 g, 91%.

$^1$HNMR (CDCl$_3$) δ: 0.90 (t, 3H), 1.35 (m, 6H), 1.65 (quin, 2H), 2.35 (t, 2H), 3.90 (m, 2H), 4.0 (m, 2H), 5.15 (m, 4H), 5.75 (m, 2H).

Ir vmax (thin film): 2933, 2861, 2338, 1722, 1655, 1563, 1466, 1415, 1227, 1114, 995, 923 cm$^{-1}$.

EXAMPLE 28

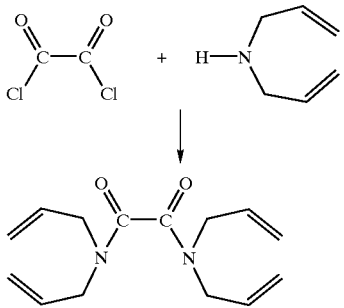

Oxalyl Chloride (25.0 g, 0,197 mol) was placed in dry dichloromethane (150 cm$^3$) and cooled to −5° C. and stirred. The diallylamine (48.6 g, 0.50 mol) in dry dichloromethane (50 cm$^3$) was slowly added dropwise (much HCl evolved!) keeping temperature below 20° C. After addition the solution was stirred at room temperature for thirty minutes and then washed with 3N HCl (100 cm$^3$), saturated K$_2$CO$_3$ (100 cm$^3$), brine (100 cm$^3$), and finally dried over MgSO$_4$. Removal of solvent left a brown oil (one spot by tlc, silica gel/EtOAc). The oil was passed through a silica gel column using ethyl acetate as the eluent. Removal of solvent left a yellow oil. 42.50 g, 87%.

$^1$HNMR (CDCl$_3$) δ: 3.85 (m, 4H), 4.0 (m, 4H), 5.15 (m, 8H), 5.80 (m, 4H).

Ir vmax (thin film): 308.8, 2991, 1654, 1488, 1413, 1285, 1215, 1128, 996, 930, 783, 720 cm$^{-1}$.

EXAMPLE 29

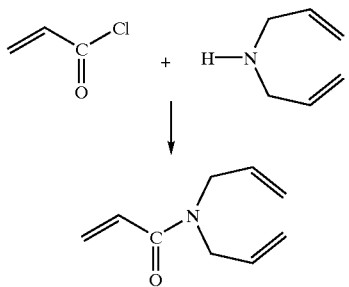

Acryloyl chloride (25.0 g, 0.28 mol) was placed in dry dichloromethane (150 cm$^3$) and cooled to −5° C. in a salt/ice bath and stirred. The diallylamine (29.15 g, 0.30 mol) in dry dichloromethane (50 cm$^3$) was-added dropwise over ~1 h* and the resultant solution allowed to rise to room temperature and stirred for 30 minutes. The solution was treated with 3N HCl (100 cm$^3$) saturated K$_2$CO$_3$ solution (100 cm$^3$) and brine (100 cm$^3$) then dried over MgSO$_4$. Removal of solvent gave a brown oil. The oil was passed through a silica gel column using ethyl acetate as eluent. Removal of solvent gave a yellow oil 37.1 g 89%.

\* evolution of HCl

Ir vmax (thin film).: 2988, (1726), 1657, 1618, 1470, 1443, 1226, 1196, 1077, 989, 926, 795 cm$^{-1}$.

$^1$HNMR (CDCl$_3$) δ: 3.95, (d, 2H), 4.05 (d, 2H), 5.15 (m, 4H), 5.65 (m, 1H), 5.75 (m, 2H), 6.90 (m, 2H).

EXAMPLE 30

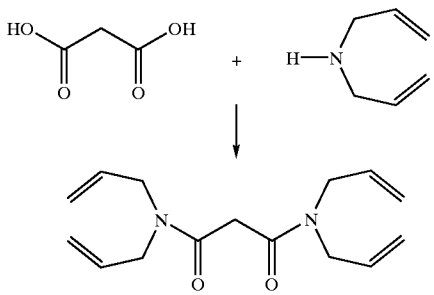

Malonic acid (16.23 g, 0.156 mol), diallylamine (31.1 g, 0.320 mol) and 1,3-dicyclohexylcarbodiimide (66.0 g, 0.320 mol) were placed in dry dichloromethane and the mixture stirred for 18 hours at room temperature. The copious quantity of 1,3-dicyclohexyl-urea was removed by filtration (Whatman No. 1 filter paper) and the organic filtrate washed with 3N HCl (150 cm$^3$), then saturated potassium carbonate followed by water (150 cm$^3$) The solution was dried over MgSO$_4$ and removal of solvent gave a brown oil. The oil was passed through a silica gel column using ethyl acetate as eluent. Further decoloration was achieved using charcoal and dichloromethane/40/60 petrol (1:1) as solvent. Filtration and removal of solvent in vacuo gave a yellow/brown oil. 33.70 g, 87%.

$^1$HNMR (CDCl$_3$) δ: 3.55 (s, 2H), 4.04 (d, 8H), 5.15 (m, 8H), 5.80 (m, 4H).

Ir vmax (thin film): 2987, 2934, 1652, 1414, 1310, 1223, 1193, 1136, 996, 922, 852, 700, 556 cm$^{-1}$.

EXAMPLE 31

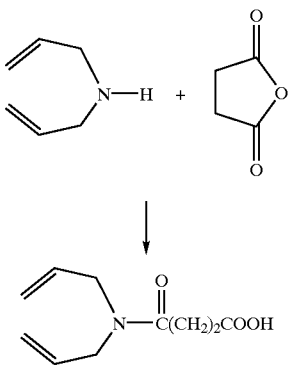

Succinic anhydride (50.0 g, 0.5 mol) was placed in a dry dichloromethane (400 cm$^3$) and stirred and cooled to −5° C. in a salt/ice bath. Diallylamine (48.6 g, 0.5 mol) in dry dichloromethane (100 cm$^3$) was added dropwise over 1 hour keeping the temperature at >20° C. As addition proceeded, the succinic anhydride, suspended in dichloromethane became less evident until all had reacted to form a pale yellow solution. The solution was washed in 3N HCl solution (200 cm³), saturated K₂CO₂ (200 cm³) then water (200 cm³) and finally dried over MgSO₄. Removal of solvent left a light yellow oil (of one spot purity on t.l.c.). 95.46 g, 96%.

¹HNMR (CDCl₃) δ: 2.65 (m, 4H), 3.95 (d, 2H), 4.05 (d, 2H), 5.15 (m, 4H), 5.75 (m, 2H).

Ir νmax (thin film): 3088 (br), 1737, 1650, 1480, 1418, 1233, 1176, 995, 928, 829, 558 cm⁻¹.

EXAMPLE 32

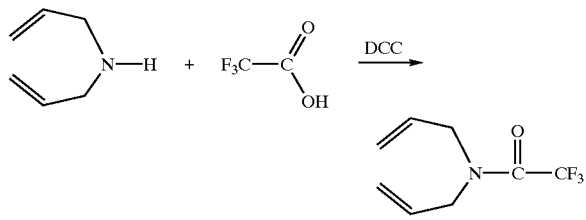

Diallylamine (17.0 g, 0.185 mol) and 1,3-dicyclohexylcarbodiimide (36.12 g, 0.175 mol) were dissolved in dry dichloromethane (150 cm³) and the solution cooled to 0° C. Trifluoroacetic acid (20.0 g, 0.175 mol) in dry dichloromethane (50 cm³) was added dropwise over 1 hour and the whole was left stirring at room temperature for 72 hours. The 1,3-dicyclohexylurea was removed by filtration and the solvent removed in vacuo to leave a yellow oil. Column chromatography (silica gel—dichloromethane) followed by removal of solvent in vacuo gave a pale yellow oil which crystallised slowly on standing. 26.67 g, 79.0%.

¹HNMR (CDCl₃) δ: 4.0 (d, 4H), 5.20 (m, 4H), 5.75 (m, 2H).

Ir νmax (thin film): 2935, 2866, 1698, 1559, 1454, 1348, 1305, 1160, 1050, 994, 926, 895 cm⁻¹.

EXAMPLE 33

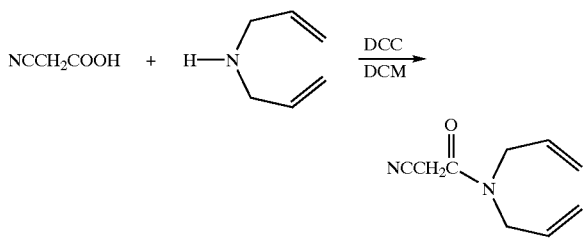

Cyanoacetic acid (25.0 g, 0.294 mol) in dry dichloromethane (100 cm³) was added dropwise to a solution of diallylamine (29.0 g, 0.30 mol) and 1,3-dicyclohexylcarbodiimide (64.0 g, 0.31 mol) in dry dichloromethane (250 cm³). The mixture was left stirring for 15 hours at room temperature. The 1,3-dicyclohexylurea was removed by filtration and the solvent removed to leave a brown oil. Column chromatography (silica gel—dichloromethane) followed by removal of solvent in vacuo left a light yellow oil. 40.50 g, 84%.

¹HNMR (CDCl₃) δ: 3.75 (s, 2H), 4.0 (d, 2H), 4.10 (d, 2H), 5.40 (m, 4H), 5.90 (m, 2H).

Ir νmax (thin film): 3091, 2931, 2261, 1674, 1448, 1316, 1229, 1192, 1139, 996, 931, 820 cm⁻¹.

EXAMPLE 34

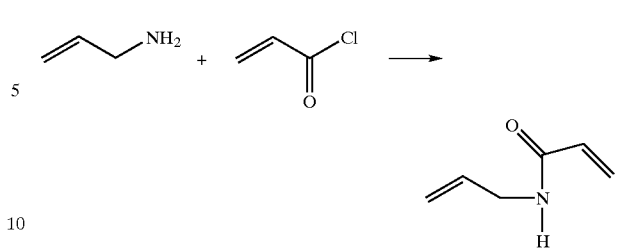

Acryloyl Chloride (16.5 g, 0.180 mol) was dissolved in dry dichloromethane (50 cm³) and the solution was cooled to −5° C. in a salt/ice bath and stirred. The allylamine (5.0 g, 0.087 mol) in dry dichloromethane (25 cm³) was added dropwise over 30 minutes and the resultant solution was allowed to rise to room temperature and stirred for a further 30 minutes. The solution was treated with 3M HCl (50 cm³), saturated K₂CO₃ solution (50 cm³) and brine (50 cm³) then dried over MgSO₄. Removal of solvent gave a yellow oil. The oil was passed through a silica gel column using ethyl acetate as the eluent. Removal of solvent gave a yellow oil. 8.90 g, 92%.

¹HNMR (CDCl₃) δ: 3.95 (t, 2h), 5.15 (m, 2h), 5.60 (m, 1h), 5.85 (m, 1h), 6.20 (m, 2h), 6.70 (s, br, 1H).

Ir νmax (thin film): 3289, 3084, 1664, 1628, 1549, 1412, 1246, 1070, 989, 922, 808 cm⁻¹.

EXAMPLE 35

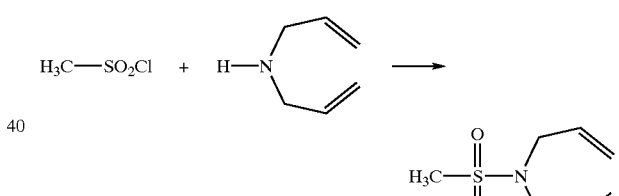

Methane sulphonyl chloride (10.0 g, 0.087 mol), diallyamine (8.75 g, 0.090 mol) and potassium carbonate (10 g) were placed in sieve-dried butanone (100 cm³) and the mixture was refluxed with stirring for 3 hours. Thin layer chromatography (ethyl acetate) showed a product spot at ~Rf 0.5 with no evidence of diallyamine remaining. The reaction mixture was filtered (Whatman No. 1 filter paper) and the solvent was removed in vacuo to leave a brown oil. The oil was purified using column chromatography using silica gel and ethyl acetate-petrol 40/60 (1:1) as eluent. Removal of solvent in vacuo gave the product as a yellow oil (12.30 g, 80%)

Ir νmax (thin film): 3089, 2990, 1331 (s), 1150, 1046, 996, 934,793, 733 cm⁻¹;

¹HNMR (CDCl₃) δ: 2.90 (s,3H), 3.85 (d, 4H)m 5.2 (m,4H), 5.80 (m,2H).

The compounds of each of Examples 24 −35 above had the properties of a u.v. curable adhesive.

EXAMPLE 36

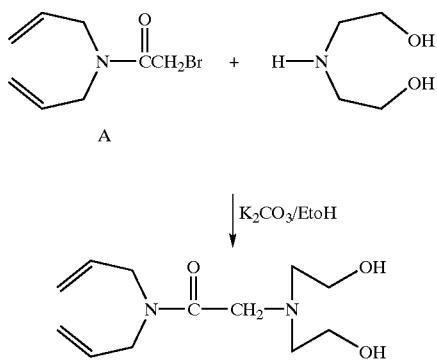

Amide A (5.0 g, 0.023 mol), diethanolamine (2.40 g, 0.023 mol) and potassium carbonate (3.45 g (0.025 mol) in ethanol (50 cm3) were stirred together at reflux for 15 h. The solids were removed by filtration (Whatman No. 1) and the solvent removed in vacuo to leave a brown oil. Column chromatography (silica gel/ethyl acetate) followed by removal of solvent in vacuo and thorough drying left 4.8 g, 87% as a yellow oil.

Ir vmax (thin film): 3650–3100, 2937, 1646 (S), 1419, 1354, 1229, 1131, 995, 927, 754 cm$^{-1}$.

$^1$HNMR (CDCl$_3$) δ: 2.80 (t, 2H), 3.40 (t, 2H), 3.50 (s, 2H), 3.90 (d, 2H), 4.0 (d, 2H), 5.15 (m, 4H), 5.85 (m, 2H).

EXAMPLE 37

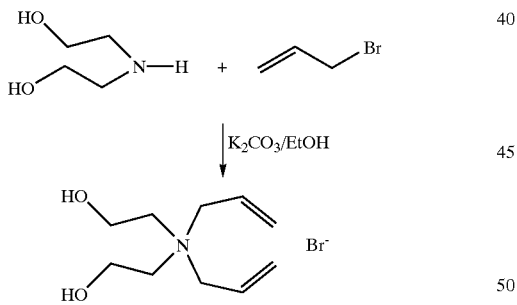

Diethanolamine (10.0 g, 0.095 mol), allyl bromide (24.2 g, 0.20 mol) and potassium carbonate (34.5 g, 0.25 mol) were placed in ethanol (150 cm$^3$) and the mixture was warmed to 65–70° C. with stirring and kept at this temperature for 15 h. Solids were removed by filtration and the solvent removed in vacuo to leave a yellow oil, 21.7 g, 86%.

Ir vmax (thin film): 3600–3100 (s), 2980, 1647, 1457, 1366, 1090, 955, 754 cm$^{-1}$.

$^1$HNMR (CDCl$_3$) δ: 3.62 (s, 2H), 3.78 (d, 2H), 3.98 (s, 2H), 4.10 (m, 4H), 4.24 (m, 4H), 5.24 (m, 4H), 6.10 (m, 2H).

EXAMPLE 38

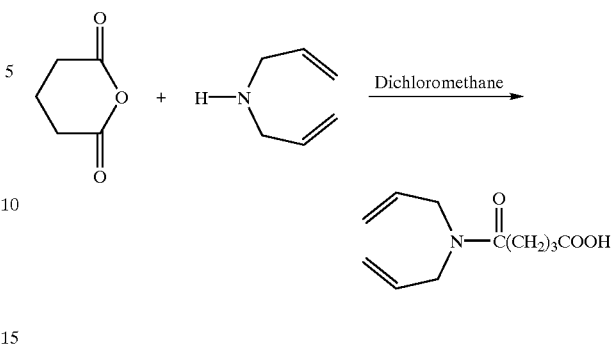

Glutaric anhydride (30.0 g, 0.26 mol) was placed in dry dichloromethane (150 cm$^3$) and the mixture cooled (salt/ice bath) and stirred. Diallylamine (27.20 g, 0.28 mol) in dry dichloromethane (50 cm$^3$) was added dropwise to form a clear yellow solution which was stirred for a further 30 min. It was then washed with 3N HCl (200 cm3) then brine (200 cm3) and dried over MgSO4. Removal of solvent left a yellow oil, 53.7 g, 98%.

Ir vmax (thin film): 2500–3600, 1715, 1605, 1640, 1480, 1410, 1215, 995, 920 cm$^{-1}$.

$^1$HNMR (CDCl$_3$) δ: 1.95 (quin, 2H), 2.45 (m, 4H), 3.90 (d, 2H), 3.98 (d, 2H), 5.15 (m, 4H), 5.75 (m, 2H), 11.10 (s, 1H).

EXAMPLE 39

Bromoacetyl bromide (30.0 g, 0.15 mol) was dissolved in dry dichloromethane (200 cm$^3$) and the solution stirred at room temperature. Diallylamine (14.50 g, 0.15 mol) in dry dichloromethane (50 cm$^3$) was added dropwise with much evolution of HCl gas, after complete addition the solvent was removed in vacuo to give a brown oil. Column chromatography (silica gel/ethyl acetate) followed by removal of solvent gave a yellow oil, 31.4 g, 97%.

Ir vmax (thin film): 3513, 3087, 2989, 2927, 1657, 1449, 1343, 1257, 1212, 1108, 994, 922, 728, 689, 618, 555 cm$^{-1}$.

$^1$HNMR (CDCl$_3$) δ: 3.85 (s, 2H), 3.95 (m, 4H), 5.20 (m, 4H), 5.80 (m, 2H).

EXAMPLE 40

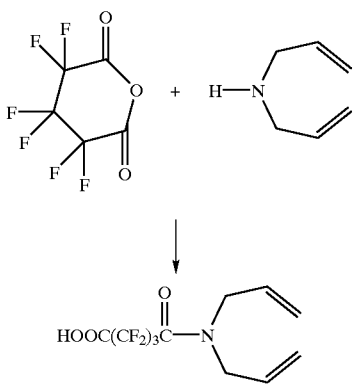

Hexafluoroglutaric anhydride (5.0 g, 0.0225 mol) was dissolved in dry dichloromethane (100 cm$^3$) and the solution was cooled to ~–5° C. in a salt/ice bath. Diallylamine (2.20 g, 0.022 mol) in dry dichloromethane (20 cm$^3$) was added dropwise over 15 minutes and the mixture stirred for 30 minutes at room temperature. Aqueous HCl (6N) (100 cm3) was added and the mixture stirred for 10 minutes. The organic layer was separated and dried over MgSO4. Removal of solvent gave a brown oil, 5.50 g, 77%.

Ir vmax (thin film): 3095, 3650–2500, 1786, 1678 (s), 1422, 1244, 1164, 1052, 993 cm$^{-1}$.

$^1$HNMR (CDCl$_3$) δ: 3.67 (~1H, 4.0 (d, 2H), 4.05 (d, 2H), 5.25 (m, 4H), 5.76 (m, 2H), 12.0 (s, 1H), 5.43 (s~½H), 5.46 (d, ~½H)

EXAMPLE 41

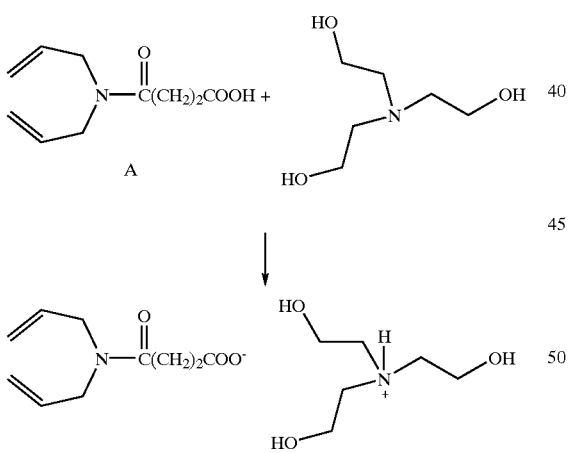

Amide A (5.0 g, 0.0254 mol) and triethanolamine (3.78, 0.0254 mol) were dissolved in dry dichloromethane (100 cm$^3$) and stirred at room temperature for 1 hr. The solvent was removed in vacuo to leave a pale yellow oil (8.78 g, 100%) which was not purified since both of the starting materials were 98–100% pure.

$^1$HNMR (CDCl$_3$) δ: 2.55 (m, 2H), 2.60 (m, 2H), 2.98 (t, 6H), 3.75 (t, 6H), 3.95 (m, 4H), 5.15 (m, 1H), 5.76 (m, 2H), 6.32 (s, br, 4H).

Ir vmax (thin film): 3363 (s), 3156, 2936, 1639 (s), 1579 (s), 1409, 1249, 1080, 1032, 1003, 918, 563 cm$^{-1}$.

EXAMPLE 42

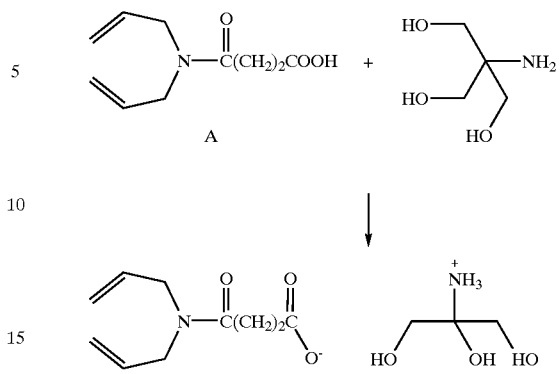

Amide A (5.0 g, 0.0254 mol) and tris(hydroxymethyl) aminoethane (3.08 g, 0.0254 mol) were placed together in dry dichloromethane (100 cm3) and the combination stirred for 1 h at room temperature. The solvent was removed in vacuo to leave a pale yellow oil which was not further purified since both starting materials were 98–100% pure. Yield 8.08 g, 100%.

$^1$HNMR (CDCl$_3$) δ: 2.40 (s, br, 2H), 2.60 (s, br, 2H), 3.75 (s, br, 8H), 3.95 (s, br, 2H), 5.15 (m, 4H), 5.70 (m, 2H), 6.85 (s, br, 6H, —OH$_1$+NH).

Ir vmax (thin film): 3392, 1561, 1463, 1407, 1221, 1190, 1063, 933, 565 cm$^{-1}$.

EXAMPLE 43

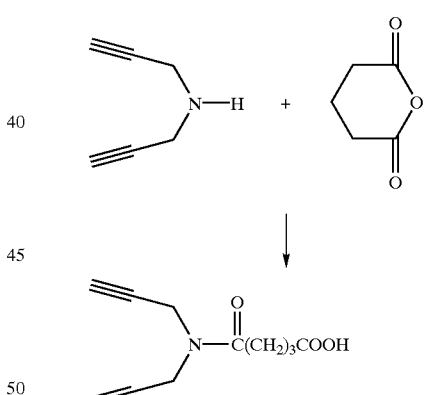

Glutaric anhydride (3.68 g, 0.032 mol) was placed in dry dichloromethane (100 cm$^3$) but did not dissolve. Dipropargylamine (3.00 g, 0.032 mol) in dry dichloromethane (25 m$^3$) was added slowly dropwise with a rise in temperature due to an exothermic reaction. As addition of the dipropargylamine proceeded, the glutaric anhydride became less evident until a clear yellow reaction mixture was formed. This was left stirring for a further 1 h. The solution was washed in (i) dil (1N)(50 ml) HCl solution, (ii) NaHCO$_3$ solution (1N) (50 ml), water (50 ml), then dried over MgSO$_4$ to leave an orange coloured oil, 6.38 g, 96%.

Ir vmax (thin film): 3300, 2940, 2863, 2130, 1730 (s), 1660 (s), 1420, 1345, 1211, 1040, 956 cm$^{-1}$.

EXAMPLE 44

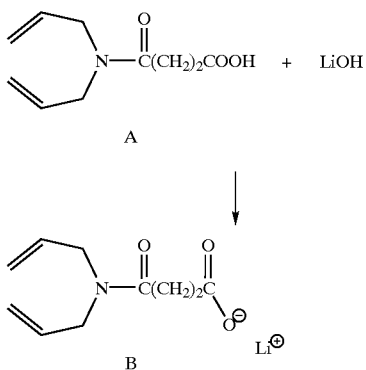

Acid A (5.0 g, 0.027 mol) and lithium hydroxide (648 mg, 0.027 mol) were dissolved in ethanol-water mixture (20 cm$^3$) Solvents were removed in vacuo to leave a white solid which was suspended in acetone. Filtration (No. 1 sinter) followed by washing of the retained solid with acetone (50 cm$^3$) and thorough drying gave the lithium salt B 4.90 g, 96%, as a white powder insoluble in most organic solvents.

Ir vmax (KBr Disc): 3085, 3020, 2980, 2922, 1643 (s), 1581 (s), 1422, 1347, 1279, 1256, 1213, 1140, 1013, 912, 833, 808, 721, 622, 575 cm$^{-1}$.

EXAMPLE 45

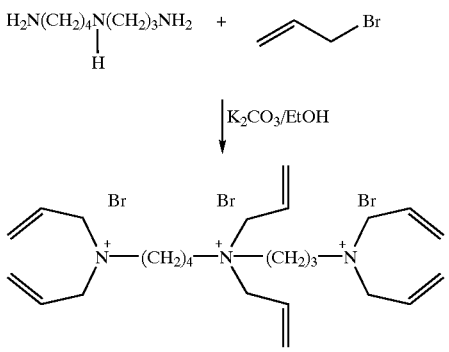

Spermidine (5.0 g, 0.035 mol), allyl bromide (34.0 g, 0.28 mol), potassium carbonate (35.0 g) and ethanol (100 cm$^3$) were refluxed for 6 h at 60° C. The solvent and excess allyl bromide were removed in vacuo to leave a brown oil, 21.0 g, 84%.

$^1$HNMR (CD$_3$OD) δ: 1.95 (m, 4H), 2.55 (quin, 2H), 3.45 (m, 8H), 4.0 (d, 8H), 4.15 (d, 8H), 5.75 (m, 16H), 6.20 (m, 8H).

Ir vmax (thin film): 2934, 2458, 1644, 1472, 1427, 1368, 1246, 995, 953, 848, 749, 662 cm$^{-1}$.

EXAMPLE 46

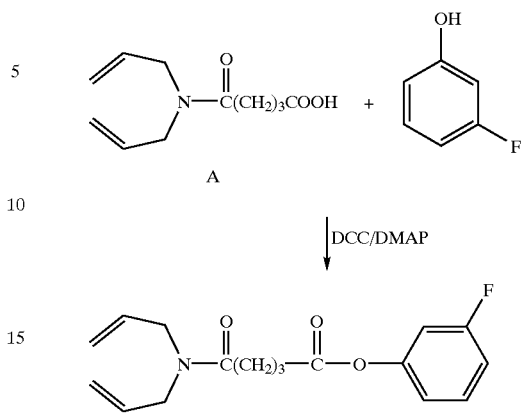

Amidoacid A (10.0 g, 0.047 mol), 3-fluorophenol (5.27 g, 0.047 mol), dicyclohexylcarbodiimide (9.70 g, 0.047 mol) and 4-dimethylaminopyridine (0.50 g) were stirred together in dry dichloromethane (150 cm$^3$) for 18 h at room temperature. The dicyclohexylurea was removed by filtration (Whatman No. 1 filter paper) and the filtrate washed with 2M KOH solution (100 cm$^3$), then water (100 cm$^3$) and dried over MgSO$_4$. Removal of solvent left a yellow oil which was purified by column chromatography (silica gel) using dichloromethane as the eluent. Removal of solvent left a clear oil, 13.4 g, 93.0%.

$^1$HNMR (CDCl$_3$) δ: 2.09 (t, 21H), 2.47 (t, 2H), 2.66 (t, 2H), 3.88 (d, 2H), 3.99 (d, 2H), 5.20 (m, 4H), 5.78 (m, 2H), 6.90 (m, 3H), 7.40 (m, 1H).

EXAMPLE 47

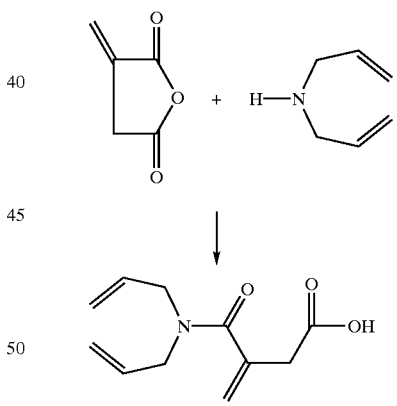

Itaconic anhydride (10.0 g, 0.09 mol) was placed in dry dichloromethane (150 cm3) and the mixture was cooled to −5° C. in a salt/ice bath. The diallylamine (9.72 g, 0.10 mol) in dry dichloromethane (50 cm$^3$) was added dropwise over 20 minutes, maintaining temperature>0° C. during addition. The mixture was stirred (during which a clear yellow solution was formed) for 1 hour. The solvent was removed in vacuo to leave a brown oil, 16.60 g, 89%.

Ir vmax (thin film): 2400–3400, 1717 (s), 1646 (s), 1620 (s), 1419, 1220, 995, 929, 842, 555 cm$^{-1}$.

$^1$HNMR (CDCl$_3$) δ: 3.35 (s, 2H), 3.92 (d, 2H), 4.10 (d, 2H), 5.2 (m, 4H), 5.70 (s, 1H), 5.75 (m, 2H), 6.35 (s, 1H), 12.40 (s.v.br, 1H).

EXAMPLE 48

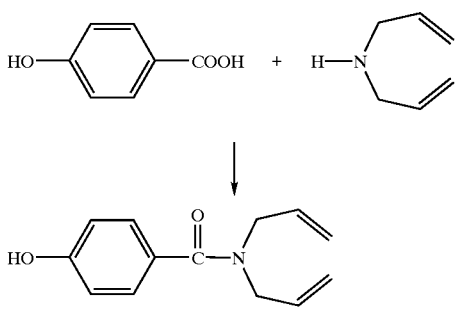

4-Hydroxybenzoic acid (10.0 g, 0.072 mol) and diallylamine (8.0 g, 0.082 mol) were dissolved in dichloromethane/tetrahydrofuran mixture (1:1) (100 cm$^3$). Dicyclohexylcarbodiimide (15.48 g, 0.075 mol) was added slowly and the mixture was stirred for 72 h. The dicyclohexylurea was removed by filtration (Whatman No. 1 filter paper) and solvents removed to leave a brown oil. The oil was dissolved in dry dichloromethane (100 cm$^3$) and the solution washed with 3M HCl solution (100 cm$^3$) and dried over MgSO$_4$. Removal of solvent left a white oily solid. Column chromatography (silica gel/EtOAc) followed by removal of solvent, gave after removal of solvent in vacuo a white powder, 14.6 g, 93%.

Ir vmax (KBr disc): 3098 (br), 2932, 2809, 1640 (w), 1573, 1447, 1281, 1241, 1174, 1112, 988, 936, 852, 748, 679, 636, 611, 575 cm$^{-1}$.

EXAMPLE 49

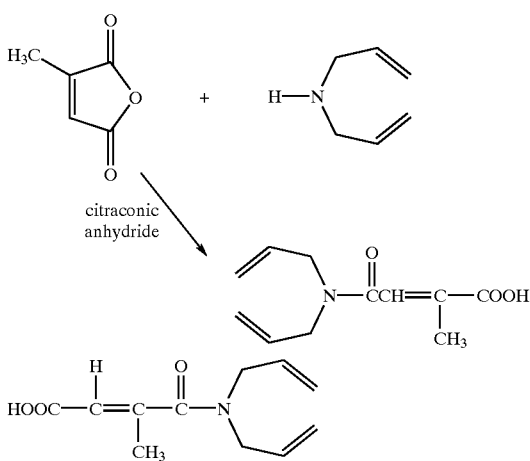

Citraconic anhydride (20.0 g, 0.178 mol) was dissolved in dry dichloromethane (300 cm3). Diallylamine (19.4 g, 0.20 mol) in dry dichloromethane (100 cm3) was added slowly dropwise over 45 minutes and stirring was continued for a further 1 h. The solvent was removed in vacuo to leave a brown oil, 34.85 g, 100%.

Ir vmax (thin film): 3600–2400, 1695 (s), 1625 (s), 1415, 1263, 1200, 1091, 997, 930, 798, 762, 661 cm$^{-1}$.

$^1$HNMR (CDCl$_3$) δ: 1.90 (s), 3.40 (d), 3.73 (d), 3.80 (d), 3.85 (d), 3.92 (d), 4.95–5.15 (m), 5.18 (d), 5.22 (d), 5.29 (d), 5.55–5.92 (complex).

EXAMPLE 50

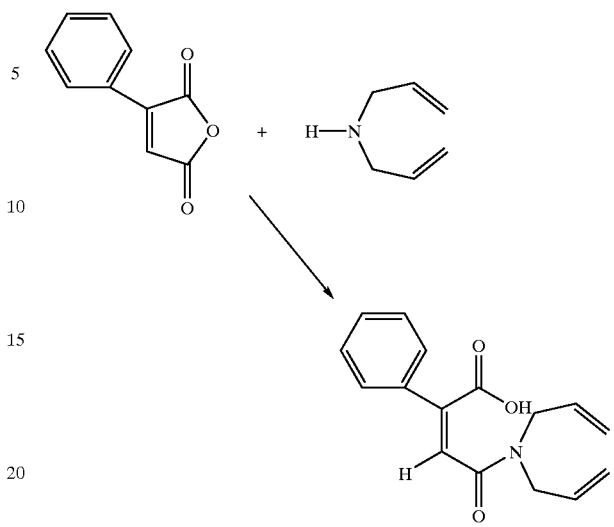

Phenylmaleic anhydride (5.0 g, 0.029 mol) was dissolved in dry dichloromethane (100 cm$^3$) and stirred. Diallylamine (3.40 g, 0.035 mol) in dry dichloromethane (20 cm$^3$) was added slowly dropwise over 10 minutes and stirring was continued for a further 1 h. The solvent was removed in vacuo and the residual brown oil thoroughly dried. 7.30 g, 94%. The oil solidified on standing.

Ir vmax (thin film): 3600–2500, 1625 (s), 1700, 1420, 1363, 1200, 1091, 997, 930, 798, 762, 660 cm$^{-1}$.

$^1$HNMR (CDCl$_3$) δ: 3.60 (d, 3.70 (d), 4.10 (d), 5.0 (m), 5.20 (m), 5.45 (m), 5.90 (m), 7.40 (m), 7.55 (m).

EXAMPLE 51

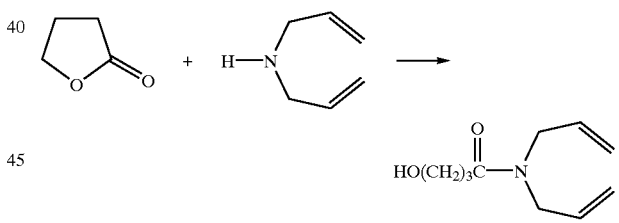

Gamma butyrolactone (5.00 g, 0.06 mol) and diallylamine (5.83 g, 0.06 mol) were mixed together (no solvent) and heated (60° C.) for 24 h. Thin layer chromatography (EtOAc) showed predominantly a new single product spot at ~Rf 0.25. The reaction mixture was dissolved in dry dichloromethane (100 cm$^3$) and washed with 3N HCl (50 cm$^3$), 3N K$_2$CO$_3$ solution (50 cm;) and then brine (50 cm$^3$). Finally, the solution was dried over MgSO$_4$. The solvent was removed in vacuo and the residual brown oil purified using column chromatography (silica gel, ethyl acetate) to give after removal of solvent in vacuo, and thorough drying 7.4 g, 70%, of clear oil.

$^1$HNMR (CDCl$_3$) δ: 1.90 (quin, 2H), 2.50 (t, 2H), 3.55 (s, 1H—OH), 3.66 (t, 2H), 3.90 (d, 2H), 4.00 (d, 2H), 5.15 (m, 4H), 5.75 (m, 2H).

Ir vmax (thin film): 3420 (br, s), 3088, 2935, 1630 (s), 1417, 1359, 1283, 1239, 1138, 1063, 995, 927 cm$^{-1}$.

EXAMPLE 52

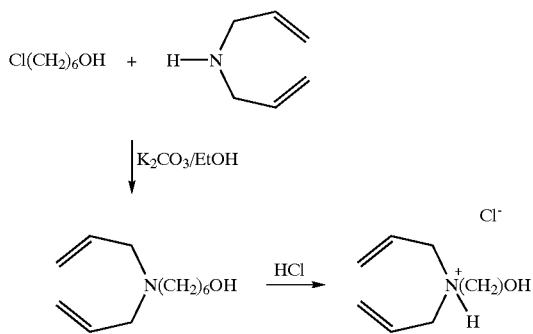

6-Chlorohexan-1-ol (10.0 g, 0.073 mol), diallylamine (7.30 g, 0.075 mol) and potassium carbonate (10.37 g, 0.075 mol) were placed in ethanol (150 cm$^3$) and refluxed for 48 h. The solvent was removed in vacuo to leave a brown oil. The oil was dissolved in dichloromethane (150 cm$^3$) and the solution was washed in brine (100 cm$^3$), then dried over Mgso$_4$. The solvent was removed in vacuo and the residual brown oil purified using column chromatography (silica gel—ethyl acetate). Removal of solvent in vacuo gave a yellow oil, 14.7 g, 99%.

$^1$HNMR (CDCl$_3$) δ: 1.40 (m, 2H), 1.50 (quin, 2H), 1.55 (quin, 2H), 2.45 (t, 2H), 2.65 (s, 1H), 3.10 (d, complex, 4H), 3.55 (t, 2H), 3.65 (quartet, 2H), 5.10 (m, 4H), 5.80 (m, 2H).

Ir vmax (thin film): 3369 (s), 2964, 2934, 1517, 1459, 1374, 1300, 1243, 1106, 1047, 1018, 826, 770 cm$^{-1}$.

EXAMPLE 53

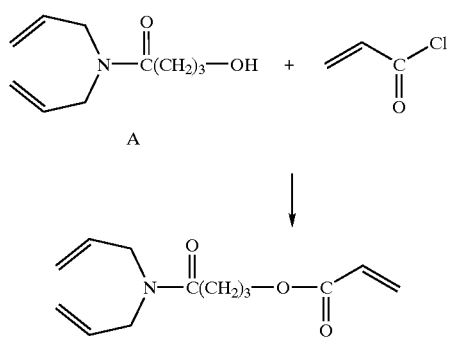

Amide A (10.0 g, 0.055 mol) was dissolved in dry dichloromethane (100 cm$^3$) the mixture was cooled in an ice bath. Acryloyl chloride (4.95 g, 0.055 mol) in dry dichloromethane (20 cm$^3$) was added dropwise over 30 minutes and the mixture was allowed to rise to room temperature. It was left stirring for 4 h. Thin layer chromatography (EtOAc) showed a new spot at ~Rf 0.6. The solvent was removed in vacuo and the product purified using column chromatography (EtOAc—40/60 petrol 1:1). Removal of solvent in vacuo gave a yellow oil 11.48 g, 89%.

Ir vmax (thin film): 2986, 1728 (s), 1645 (I), 1414, 1276, 1196, 1058, 992, 929, 813, 669 cm$^{-1}$.

$^1$HNMR (CDCl$_3$) δ: 2.10 (m, 2H), 2.45 (m, 2H), 3.90 (d, 2H), 4.0 (d, 2H), 4.2 (t, 2H), 5.20 (m, 2H), 5.75 (m, 4H), 5.80 (m, 1H), 6.15 (m, 1H), 6.45 (d, 1H).

EXAMPLE 54

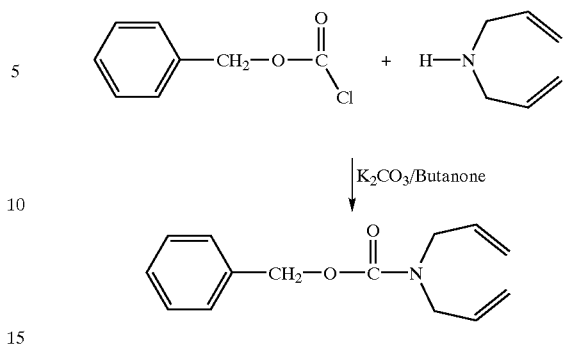

Benzyl chloroformate (10.0 g, 0.059 mol), diallylamine (5.85 g, 0.060 mol), potassium carbonate (10.0 g) in sieve dried butanone (100 cm) were stirred together at reflux temperature for 3 h. Thin layer chromatography (ethyl aetate) showed a new spot at ~Rf 0.5 and no evidence of diallylamine. The reaction mixture was filtered (Whatman No. 1 filter paper) and solvent removed in vacuo to leave a brown oil. The oil was purified using column chromatography (silica gel with ethyl acetate as eluent). Removal of solvent in vacuo left a clear yellow oil, 10.34 g, 77%.

Ir vmax (thin film): 2987, 1708 (s), 1460, 1415, 1368, 1294, 1243, 1153, 1096, 995, 926, 769, 699 cm$^{-1}$.

$^1$HNMR (CDCl$_3$) δ: 3.85 (d, 4H), 5. ((m, 4H), 5.14 (s, 2H), .5.75 (m, 2H). 7.30 (m, 5H).

EXAMPLE 55

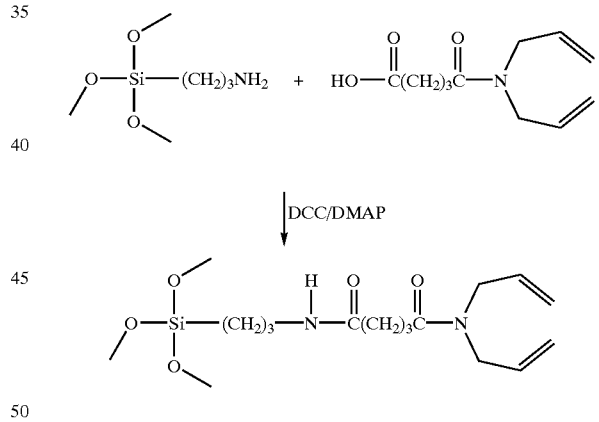

3-aminopropyltrimethoxysilane (10.0 g, 0.056 mol), 4-diallylamidobutyric Acid (11.8 g, 0.056 mol), dicyclohexylcarbodiimide (11.55 g, 0.056 mol) and 4-dimethylaminopyridine (0.5 g) were stirred at room temperature in dry dichloromethane for 72 h. The dicyclohexylurea was removed by filtration (Whatman No. 1 filter paper) and solvent removed to leave a yellow oil. The oil was passed through a short column of neutral aluminium followed by ethyl acetate (500 cm$^3$). Removal of solvent left a clear colourless oil 16.8 g, 80%.

Ir vmax (thin film): 3314, 2940, 2120, 1650 (s), 1547, 1417, 1229, 1086, 994, 927, 808, 754, 666 cm$^{-1}$.

$^1$HNMR (CDCl$_3$) δ: 0.65 (t, 2H), 1.95 (quin, 2H), 2.25 (t, 2H), 2.40 (t, 2H), 3.20 (quin, 2H), 3.55 (s, 9H), 3.90 (d, 2H), 4.0 (d, 2H), 5.10 (m, 4H), 5.75 (m, 2H), 6.5 (d, 2H).

EXAMPLE 56

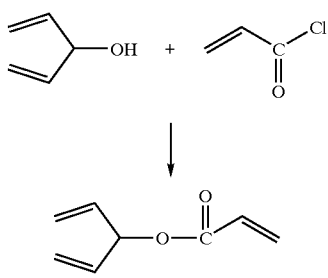

1,4-Pentadien-3-ol (5.0 g, 0.060 mol) and acryloyl chloride (5.43 g, 0.060 mol) were dissolved in dry acetone. Potassium carbonate (10 g) was added and the mixture was stirred at reflux for 15 h. The solids were removed by filtration (Whatman No. 1 filter paper) and the solvent removed in vacuo to leave a yellow oil. Chromatography using flash silica gel with ethyl acetate as the eluent gave, after thorough drying in vacuo, etc. 6.43 g, 78% of pale yellow oil.

Ir vmax (thin film): 2935, 1736 (s), 1653, 1618, 1411, 1186, 1090, 989, 931, 810 cm$^{-1}$.

$^1$HNMR (CDCl$_3$) δ: 5.10–5.45 (m, 5H), 5.70–5.95 (m, 3H), 6.20 (m, 1H), 6.45 (m, 1H).

EXAMPLE 57

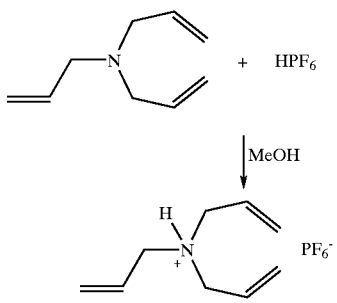 + HPF$_6$

↓ MeOH

Triallylamine (20.0 g) was dissolved in methanol and stirred at room temperature. 6N hexafluorophosphoric acid in methanol (from 65% solution in H$_2$O) was added to pH 2.0 and the pink solution was left stirring for 15 minutes. The solvents (MeOH and H$_2$O) were removed in vacuo to leave a pink coloured oil. The oil was re-dissolved in dry dichloromethane and the solution was dried over MgSO$_4$. It was then filtered (Whatman No. 1 filter paper+"Hyflo"). Removal of solvent in vacuo gave a clear, pink coloured oil, 35.4 g, 85%.

Ir vmax (thin film): 2997, 2543, 1459, 1429, 1289, 1244, 1143, 1056, 997, 953, 841 (s), 756, 661 cm$^{-1}$.

$^1$HNMR (CDCl$_3$) δ: 3.65 (s, 6H), 5.55 (m, 6H), 6.0 (m, 3H), 10.55 (s, br, 1H).

What is claimed is:

1. Method for producing a polymeric material, said method comprising subjecting a starting material which comprises a group of sub-formula (I)

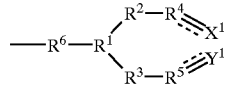

where R$^1$ is CR$^a$ where R$^a$ is hydrogen or alkyl, and R$^6$ is a bond, or R$^1$ and R$^6$ together form an electron withdrawing group wherein either (i)R$^1$ is a group N$^+$R$^{12}$(Z$^{m-}$)$_{1/m}$, S(O)$_p$R$^{13}$, B, P(O)$_q$R$^{14}$ or Si(R$^{15}$) where R$^{12}$, R$^{13}$, R$^{14}$ and R$^{15}$ are independently selected from hydrogen or hydrocarbyl, Z is an anion of charge m, p is 0, 1 or 2, and q is 1 or 2; and R$^6$ is a bond; or (ii) R$^1$ is a nitrogen atom and R$^6$ is C(O) or S(O)$_2$; or (iii) R$^1$ is a CH group and R$^6$ is a group OC(O), C(O) or S(O)$_2$;

R$^2$ and R$^3$ are independently selected from (CR$^7$R$^8$)$_n$, or a group CR$^9$R$^{10}$, CR$^7$R$^8$CR$^9$R$^{10}$ or CR$^9$R$^{10}$CR$^7$R$^8$ where n is 0, 1 or 2, R$^7$ and R$^8$ are independently selected from hydrogen or alkyl, and either one of R$^9$ or R$^{10}$ is hydrogen and the other is an electron withdrawing group given by nitrile, trifluoromethyl, acyl or nitro, or R$^9$ and R$^{10}$ together with the carbon atom to which they are attached form an electron withdrawing group given by carbonyl R$^4$ and R$^5$ are independently selected from CH or CR$^{11}$ where R$^{11}$ is an acyl, nitrile or nitro electron withdrawing group;

the dotted lines indicate the presence or absence of a bond, and X$^1$ is a group CX$^2$X$^3$ where the dotted line bond to which it is attached is absent and a group CX$^2$ where the dotted line bond to which it is attached is present, Y$^1$ is a group CY$^2$Y$^3$ where the dotted line bond to which it is attached is absent and a group CY$^2$ where the dotted line bond to which it is attached is present, and X$^2$, X$^3$, Y$^2$ and Y$^3$ are independently selected from hydrogen and fluorine;

provided that at least one of (a) R$^1$ and R$^6$ or (b) R$^2$ and R$^3$ or (c) R$^4$ and R$^5$ includes an electron withdrawing group which is able to activate a cyclopolymerization reaction; to suitable conditions under which a cyclopolymerization reaction will occur, subject to the following further provisos:

(i) that the starting material is other than triallyamine hydrochloride;

(ii) that when R$^1$ and R$^6$ together form the sole electron withdrawing group and R$^1$ is a group N$^+$R$^{12}$(Z$^{m-}$)$_{1/m}$, where R$^{12}$ is hydrogen or hydrocarbyl, Z is an anion of charge m and R$^6$ is a bond, said conditions are subjecting the compound to radiation in the substantial absence of a solvent or sulphur dioxide gas; and (iii) that where R$^1$ and R$^6$ together form the sole electron withdrawing group and R$^1$ is CH and R$^6$ is OC(O), then the compound does not further contain a mesogenic group, or contains at least one further group of sub-formula (I).

2. A method according to claim 1 wherein the group of sub-formula (I) is a group of sub-formula (IA)

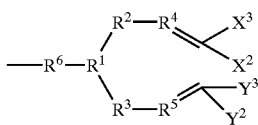  [IA]

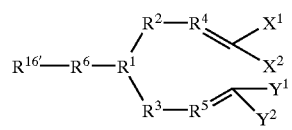  [III]

where $R^1$, $R^2$, $R^3$, $R^4$, $R^5$, $R^6$, $X^2$, $X^3$, $Y^2$ and $Y^3$ are as defined in claim 1.

3. A method according to claim 1 wherein at least $R^1$ and $R^6$ together form an electron withdrawing group.

4. A method according to claim 1 wherein the conditions under which a polymerisation reaction will occur is the application of radiation, where necessary in the presence of a photoinitiator.

5. A method according to claim 4 wherein the polymerisation is effected by the application of ultraviolet or thermal radiation.

6. A method according to claim 5 wherein the radiation is ultraviolet radiation.

7. A method according to claim 1 wherein $R^1$ is $N^+R^{12}(Z^{m-})_{1/m}$, $S(O)_pR^{13}$, B, $P(O)_qR^{14}$ or $Si(R^{15})$ where $R^{12}$, $R^{13}$, $R^{14}$ and $R^{15}$ are independently selected from hydrogen or hydrocarbyl, Z is an anion of charge m, p is 0, 1 or 2, and q is 1 or 2; and $R^6$ is a bond.

8. A method according to claim 7 wherein $R^1$ is a group $N^+R^{12}(Z^{m-})_{1/m}$, and $R^6$ is a bond.

9. A method according to claim 7 wherein Z is a halide ion, a boride ion or a carboxylic acid ester.

10. A method according to claim 4 where $R^1$ is a nitrogen atom and $R^6$ is a group such that $R^1$ and $R^6$ form an electron withdrawing group.

11. A method according to claim 10 where $R^1$ and $R^6$ together form an amide group, where $R^1$ is a nitrogen atom and $R^6$ is $C(O)$—, —$S(O)_2$—, —$C(O)O$—, —$CH_2O$—, or a group —CH=CH—$R^a$— where $R^a$ is an electron withdrawing group.

12. A method according to claim 11 wherein $R^6$ is a carbonyl group or sulphonyl group.

13. A method according to claim 11 wherein $R^6$ is a group —CH=CH—$R^a$— where $R^a$ is a carbonyl group or phenyl substituted at the ortho and/or para positions by an electron withdrawing substituent such as nitro.

14. A method according to claim 7 wherein the conditions used to effect polymerisation is the presence of a chemical initiator or an electron beam.

15. A method according to claim 1 where in the group of sub-formula (I) $X^1$ and $Y^1$ represent $CX^2X^3$ and $CY^2Y^3$ respectively, the dotted bonds are absent and $X^2$, $X^3$, $Y^2$ and $Y^3$ are all hydrogen.

16. A method according to claim 1 wherein the starting material is a compound of structure (II)

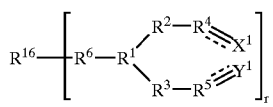  [II]

where $X^1$, $Y^1$, $R^1$, $R^2$, $R^3$, $R^4$, $R^5$, $R^6$ and the dotted bonds are as defined in claim 1, r is an integer of 1 or more, and $R^{16}$ is a bridging group, an optionally substituted hydrocarbyl group, a perhaloalkyl group or an amide, of valency r.

17. A method according to claim 16 wherein the starting material comprises a compound of formula (III)

where $X^1$, $X^2$, $Y^1$, $Y^2$, $R^1$, $R^2$, $R^3$, $R^{14}$, $R^5$ and $R^6$ are as defined in claim 1, $R^{16'}$ is an optionally substituted hydrocarbyl group, a perhaloalkyl group or an amide.

18. A method according to claim 17 wherein the compound of formula (III) is a compound of formula (IV)

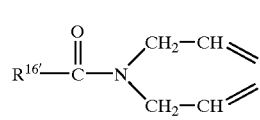  [IV]

where $R^{16'}$ is as defined in claim 17 or a compound of formula (VI)

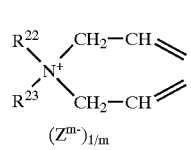  [VI]

$(Z^{m-})_{1/m}$ where Z and m are as defined in claim 1, $R^{22}$ and $R^{23}$ are independently selected from hydrogen and hydrocarbyl, such as alkyl and alkenyl, in particular prop-2-enyl or hydroxyethyl.

19. A method according to claim 1 for the production of a homopolymer.

20. A method according to claim 1 when used in the production of a copolymer where the starting materials are mixed with different monomeric units.

21. A method according to claim 1 wherein the starting material is applied to a substrate prior to polymerisation and the polymerisation reaction results in the production of a coating on the substrate.

22. A method of preparing a compound of formula (II) as defined in claim 16 which comprises reacting a compound of formula (XV)

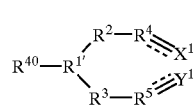  [XV]

where $X^1$, $Y^1$, $R^2$, $R^3$, $R^4$, $R^5$ and the dotted bonds are as defined in claim 1, $R^{1'}$ is a group $R^1$ as defined in claim 1 or a precursor thereof, and $R^{40}$ is hydrogen or hydroxy, with a compound of formula (XVI)

$R^{16}$—[$R^6$—$Z^4$]$_r$  (XVI)

where $R^6$, $R^{16}$ and r is as defined in relation to formula (II) and $Z^4$ is a leaving group, and thereafter if necessary, converting a precursor group $R^{1'}$ to a group $R^1$.

23. A polymer obtained by a method according to claim 1.

24. A polymer comprising the product of a polymerisation of a compound of formula (III) as defined in claim 17.

25. A novel compound of formula (II) as defined in claim 16.

* * * * *

UNITED STATES PATENT AND TRADEMARK OFFICE
CERTIFICATE OF CORRECTION

PATENT NO. : 6,559,261 B1
APPLICATION NO. : 09/743901
DATED : May 6, 2003
INVENTOR(S) : Milne et al.

Page 1 of 1

It is certified that error appears in the above-identified patent and that said Letters Patent is hereby corrected as shown below:

Title page, item (75) Inventors should read as follows:

Paul E. Milne, Malvern (GB); Keith M. Blackwood, Bracknell (GB); Steven M. Kelly, Hull (GB); Alan W. Hall, Hull (GB); John W. Goodby, Hull (GB)

Signed and Sealed this

Third Day of November, 2009

David J. Kappos
*Director of the United States Patent and Trademark Office*